(12) United States Patent
Celermajer et al.

(10) Patent No.: US 11,986,188 B2
(45) Date of Patent: *May 21, 2024

(54) IMPLANTABLE DAMPING DEVICES FOR TREATING DEMENTIA AND ASSOCIATED SYSTEMS AND METHODS OF USE

(71) Applicant: The Brain Protection Company PTY LTD, Paddington (AU)

(72) Inventors: David Stephen Celermajer, Vaucluse (AU); Anthony John Ujhazy, East Lindfield (AU); Michael Wallace, Pleasanton, CA (US); Zoran Milijasevic, Bayview (AU); Johnathon Choi, West Pennant Hills (AU); Jarred Shein, Bondi Beach (AU)

(73) Assignee: THE BRAIN PROTECTION COMPANY PTY LTD, Paddington (AU)

( * ) Notice: Subject to any disclaimer, the term of this patent is extended or adjusted under 35 U.S.C. 154(b) by 215 days.

This patent is subject to a terminal disclaimer.

(21) Appl. No.: 17/541,448

(22) Filed: Dec. 3, 2021

(65) Prior Publication Data

US 2022/0233200 A1 Jul. 28, 2022

Related U.S. Application Data

(63) Continuation of application No. 15/752,211, filed as application No. PCT/AU2016/050734 on Aug. 12, 2016, now Pat. No. 11,224,433.
(Continued)

(30) Foreign Application Priority Data

Aug. 13, 2015 (AU) ................................ 2015903253

(51) Int. Cl.
*A61B 17/12* (2006.01)
*A61B 17/11* (2006.01)
(Continued)

(52) U.S. Cl.
CPC ........ *A61B 17/12109* (2013.01); *A61B 17/11* (2013.01); *A61B 17/12036* (2013.01);
(Continued)

(58) Field of Classification Search
CPC .............. A61F 2/06; A61F 2002/30289; A61F 2002/068; A61F 2230/0091; A61F 2/88;
(Continued)

(56) References Cited

U.S. PATENT DOCUMENTS 3,657,744 A  4/1972  Ersek
3,726,279 A  4/1973  Barefoot
(Continued)

FOREIGN PATENT DOCUMENTS

DE  102004018255  11/2005
EP  2586402  5/2013
(Continued)

OTHER PUBLICATIONS

European Search Report received for co-pending European Patent Application No. 16834323.4, dated Oct. 10, 2022, Applicant: The Brain Protection Company PTY Ltd, 5 pages.
(Continued)

*Primary Examiner* — Kankindi Rwego
(74) *Attorney, Agent, or Firm* — PERKINS COIE LLP

(57) ABSTRACT

Devices, systems, and methods for reducing stress on a blood vessel are disclosed herein. A damping device (100) configured in accordance with embodiments of the present technology can include an anchoring member (104) coupled to a flexible, compliant damping member (102) including a generally tubular sidewall having an outer surface (115), an
(Continued)

inner surface (113) defining a lumen configured to direct blood flow, a first end portion (106) and a second end portion (108), and a damping region (120) between the first and second end portions (106, 108). The inner and outer surfaces (113, 115) of the damping member (102) can be spaced apart by a distance that is greater at the damping region (120) than at either of the first or second end portions (106, 108). When blood flows through the damping member (102) during systole, the damping member (102) absorbs a portion of the pulsatile energy of the blood, thereby reducing a magnitude of the pulse pressure transmitted to a portion of the blood vessel distal to the damping device (100).

19 Claims, 17 Drawing Sheets

Related U.S. Application Data

(60) Provisional application No. 62/341,575, filed on May 25, 2016.

(51) Int. Cl.
A61F 2/06 (2013.01)
A61F 2/07 (2013.01)
A61F 2/848 (2013.01)

(52) U.S. Cl.
CPC .. *A61B 17/12136* (2013.01); *A61B 17/12172* (2013.01); *A61F 2/06* (2013.01); *A61F 2/07* (2013.01); *A61B 2017/1107* (2013.01); *A61B 2017/1132* (2013.01); *A61B 17/1214* (2013.01); *A61B 17/12181* (2013.01); *A61F 2002/068* (2013.01); *A61F 2/848* (2013.01)

(58) Field of Classification Search
CPC ......... A61F 2/848; A61B 17/11; A61B 17/12; A61B 17/12009; A61B 17/12013; A61B 17/12109; A61B 17/12136; A61B 17/12172; A61B 17/12181; A61B 17/1214; A61B 2017/1103; A61B 2017/1107; A61B 2017/111; A61B 5/021; A61B 5/026; A61L 27/50
USPC ........ 623/1.11; 601/148, 149, 150, 151, 152
See application file for complete search history.

(56) References Cited

U.S. PATENT DOCUMENTS

| | | |
|---|---|---|
| 4,881,939 A | 11/1989 | Newman |
| 5,002,531 A | 3/1991 | Bonzel |
| 5,100,429 A | 3/1992 | Sinofsky et al. |
| 5,222,980 A | 6/1993 | Gealow |
| 5,618,301 A | 4/1997 | Hauenstein |
| 5,634,895 A | 6/1997 | Igo |
| 5,665,117 A | 9/1997 | Rhodes |
| 5,702,419 A | 12/1997 | Berry |
| 5,755,777 A | 5/1998 | Chuter |
| 5,800,524 A | 9/1998 | Borghi |
| 5,800,526 A | 9/1998 | Anderson et al. |
| 5,919,224 A | 7/1999 | Thompson et al. |
| 6,010,529 A | 1/2000 | Herweck |
| 6,030,336 A | 2/2000 | Franchi |
| 6,042,605 A | 3/2000 | Martin et al. |
| 6,120,534 A | 9/2000 | Ruiz |
| 6,129,756 A | 10/2000 | Kugler et al. |
| 6,241,691 B1 | 6/2001 | Ferrera et al. |
| 6,350,282 B1 | 2/2002 | Eberhardt |
| 6,395,019 B2 | 5/2002 | Chobotov |
| 6,974,473 B2 | 12/2005 | Barclay et al. |
| 6,984,201 B2 | 1/2006 | Khaghani |
| 7,125,464 B2 | 10/2006 | Chobotov et al. |
| 7,147,661 B2 | 12/2006 | Chobotov |
| 7,575,594 B2 | 8/2009 | Sieracki |
| 7,766,814 B2 | 8/2010 | Walsh |
| 7,819,941 B2 | 10/2010 | Kunze |
| 7,981,103 B2 | 7/2011 | O'Rourke |
| 8,702,776 B2 | 4/2014 | Heltai |
| 8,708,906 B1 | 4/2014 | Orehek |
| 8,876,850 B1 | 11/2014 | Vollmers |
| 9,017,359 B2 | 4/2015 | Scandurra |
| 9,039,725 B1 | 5/2015 | Vollmers |
| 9,125,567 B2 | 9/2015 | Gross et al. |
| 9,242,082 B2 | 1/2016 | Vollmers |
| 9,492,293 B2 | 11/2016 | Richter et al. |
| 9,592,068 B2 | 3/2017 | Janardhan et al. |
| 10,064,626 B2 | 9/2018 | Celermajer et al. |
| 11,224,433 B2 | 1/2022 | Celermajer et al. |
| 2001/0027338 A1 | 10/2001 | Greenberg |
| 2002/0188341 A1 | 12/2002 | Elliott |
| 2003/0065303 A1 | 4/2003 | Wellman |
| 2003/0125797 A1 | 7/2003 | Chobotov et al. |
| 2004/0010303 A1 | 1/2004 | Bolea |
| 2004/0106971 A1 | 6/2004 | Schwartz |
| 2004/0143319 A1 | 7/2004 | Schwartz et al. |
| 2004/0147803 A1 | 7/2004 | Hegde |
| 2004/0260384 A1 | 12/2004 | Allen |
| 2005/0021023 A1 | 1/2005 | Guglielmi et al. |
| 2005/0049677 A1 | 3/2005 | Farnan |
| 2005/0055082 A1 | 3/2005 | Muvhar |
| 2006/0025852 A1 | 2/2006 | Armstrong et al. |
| 2006/0052866 A1 | 3/2006 | Gilles et al. |
| 2006/0100530 A1 | 5/2006 | Kliot et al. |
| 2006/0106449 A1 | 5/2006 | Ben Muvhar |
| 2007/0156167 A1 | 7/2007 | Connors et al. |
| 2008/0194905 A1 | 8/2008 | Walsh |
| 2009/0177279 A1 | 7/2009 | Luciano et al. |
| 2010/0030253 A1 | 2/2010 | Harris et al. |
| 2010/0056978 A1 | 3/2010 | Machan et al. |
| 2010/0256735 A1 | 10/2010 | Morales, Jr. |
| 2011/0106240 A1 | 5/2011 | Chuter |
| 2011/0144669 A1 | 6/2011 | Becking et al. |
| 2011/0166240 A1 | 7/2011 | Chuter |
| 2011/0196967 A1 | 8/2011 | Tachibana |
| 2011/0213408 A1 | 9/2011 | Gross et al. |
| 2012/0029625 A1 | 2/2012 | Chobotov et al. |
| 2012/0089218 A1 | 4/2012 | Dardi |
| 2013/0013051 A1 | 1/2013 | Benary |
| 2013/0066416 A1 | 3/2013 | Goicoechea et al. |
| 2013/0079871 A1 | 3/2013 | Scandurra et al. |
| 2013/0172981 A1 | 7/2013 | Gross |
| 2013/0218191 A1 | 8/2013 | Heltai |
| 2013/0226280 A1 | 8/2013 | O'Rourke |
| 2013/0296917 A1 | 11/2013 | Rees |
| 2014/0058436 A1 | 2/2014 | Rosenbluth et al. |
| 2014/0350658 A1 | 11/2014 | Benary |
| 2015/0025625 A1 | 1/2015 | Rylski et al. |
| 2015/0088239 A1 | 3/2015 | Ben-Muvhar |
| 2017/0042551 A1 | 2/2017 | Celermajer et al. |
| 2017/0087045 A1 | 3/2017 | Zhadkevich |
| 2017/0172771 A1 | 6/2017 | Bruckheimer et al. |
| 2017/0173262 A1 | 6/2017 | Veltz |
| 2018/0008279 A1 | 1/2018 | Celermajer et al. |
| 2018/0214157 A1 | 8/2018 | Celermajer et al. |
| 2018/0280028 A1 | 10/2018 | Orion et al. |
| 2019/0336133 A1 | 7/2019 | Celermajer et al. |
| 2019/0307459 A1 | 10/2019 | Celermajer et al. |
| 2020/0375721 A1 | 12/2020 | Celermajer et al. |
| 2021/0007839 A1 | 1/2021 | Du |
| 2021/0393189 A1 | 12/2021 | Celermajer et al. |
| 2022/0008229 A1 | 1/2022 | Celermajer et al. |
| 2022/0022881 A1 | 1/2022 | Celermajer et al. |

FOREIGN PATENT DOCUMENTS

| | | |
|---|---|---|
| JP | 5782523 | 2/2014 |
| WO | WO1996032077 | 10/1996 |
| WO | WO2001056501 | 8/2001 |
| WO | WO2003028522 | 4/2003 |
| WO | WO2004026112 | 4/2004 |

(56) References Cited

FOREIGN PATENT DOCUMENTS

| | | |
|---|---|---|
| WO | WO2004056274 | 7/2004 |
| WO | WO2005041783 | 5/2005 |
| WO | WO2005084730 | 9/2005 |
| WO | WO2006062976 | 6/2006 |
| WO | WO2007038476 | 4/2007 |
| WO | WO2008061185 | 5/2008 |
| WO | WO2012018590 | 2/2012 |
| WO | WO2012071395 | 5/2012 |
| WO | WO2013013081 | 1/2013 |
| WO | WO2013084235 | 6/2013 |
| WO | WO2014186755 | 11/2014 |
| WO | WO2004106971 | 12/2014 |
| WO | WO2016128983 | 8/2016 |
| WO | WO2017024357 | 2/2017 |
| WO | WO2018027298 | 2/2018 |
| WO | WO2018064769 | 4/2018 |
| WO | WO2018146184 | 8/2018 |
| WO | WO2020073094 | 4/2020 |
| WO | WO2020117560 | 6/2020 |
| WO | WO2020117562 | 6/2020 |

OTHER PUBLICATIONS

International Preliminary Report on Patentability received for International PCT Application No. PCT/AU2020/051377, filed Dec. 16, 2020; Applicant: The Brain Protection Company PTY Ltd; dated Mar. 29, 2022, 20 pages.

Cifuentes et al., "Hypertension Accelerates the Progression of Alzheimer-Like Pathology in a Mouse Model of the Disease," hyper.ahajournals, Jun. 2015, 7 pgs.

Cullen, et al. "Microvascular pathology in the aging human brain: Evidence that senile plaques are sites of microhaemorrhages." Neurobiology of Aging (2006) Jan. 27, 2006, pp. 1786-1796.

Ding et al., "Carotid Arterial Stiffness and Risk of Incident Cerebral Microbleeds in Older People," Arterioscler Thromb Vasc Biol, Jun. 11, 2015, 7 pgs.

Messas et al. "Arterial wall elasticity: State of the art and future prospects," Diagnostic and Interventional Imaging, (2013) 94, http://dx.doi.org/10.1016/j.diii., Jan. 2013, pp. 561-569.

Mitchell et al. "Arterial Stiffness, pressure and flow pulsatility and brain structure and function: the Age, Gene/Environment Susceptibility—Reykjavik Study," Brain (2011) 134; received Aug. 2011, 3398-3407.

Stone et al. "The Mechanical Cause of Age-Related Dementia (Alzheimer's Disease): The Brain is Destroyed by the Pulse," Journal of Alzheimer's Disease (2015) 44; accepted Sep. 2014, pp. 355-373.

International Preliminary Report on Patentability issued for International Application No. PCT/AU2016/050734, Applicant: The Brain Protection Company PTY Ltd, dated Jan. 2, 2018, 55 pages.

Takaiwa A. et al., "Changes in cognitive function during the 1-year period following endarterectomy and stenting of patients with high-grade carotid artery stenosis," Acta Neurochir, 2009, Published online Jun. 2009, vol. 151, pp. 1593-1600.

Grunwald I. Q. et al., "Influence of carotid artery stenting on cognitive function," Neuroradiology, 2010, Published online Nov. 2009, vol. 52, pp. 61-66.

Raabe R.D. et al., "One-year Cognitive Outcomes Associated with Carotid Artery Stent Placement," J Vasc Interv Radiol, 2010, vol. 21, DOI: 10.1016/j.jvir., Mar. 2010, pp. 983-988.

Lal B. K. et al., "Cognitive changes after surgery vs stenting for carotid artery stenosis," J Vasc Surg, 2011, Mar. 2011, vol. 54, pp. 691-698.

Chen Y-H et al., "Carotid stenting improves cognitive function in asymptomatic cerebral ischemia," International Journal of Cardiology, 2012, Received Jul. 2011, vol. 157, pp. 104-107.

Richard E. et al., "Prevention of dementia by intensive vascular care (preDIVA); a cluster-randomised trial in progress," Chapter 4.1 Alzheimer disease and associated disorders, Jul. 2009, pp. 46 to 58.

Dickstein D. L. et al., "Role of Vascular Risk Factors and Vascular Dysfunction in Alzheimer's Disease," Mount Sinai Journal of Medicine, 2010, Published Jan.-Feb. 2010, vol. 77, pp. 82-102.

Power M.C. et al., "The association between blood pressure and incident Alzheimer disease: a systematic review and meta-analysis," Epidemiology, 2011, Sep. 2011, vol. 22(5), pp. 646-659.

European Search Report received for co-pending European Patent Application No. 16834323.4, dated Apr. 16, 2019, Applicant: The Brain Protection Company PTY Ltd, 10 pages.

English Translation of First Office Action received for co-pending Chinese Patent Application No. 201680048180.8, dated May 13, 2019, Applicant: The Brain Protection Company PTY Ltd, 3 pages.

Examination Report received for co-pending Australian Patent Application No. 2016306711, dated Feb. 7, 2019, Applicant: The Brain Protection Company PTY Ltd, 4 pages.

International Search Report and Written Opinion issued for International Application No. PCT/US19/63294, Applicant: The Brain Protection Company PTY Ltd, dated Apr. 24, 2020, 17 pages.

International Search Report and Written Opinion issued for International Application No. PCT/US19/63309, Applicant: The Brain Protection Company PTY Ltd, dated Apr. 21, 2020, 12 pages.

International Preliminary Report on Patentability received for International PCT Application No. PCT/AU2018/051191 filed Nov. 2, 2018; Applicant: The Brain Protection Company; dated Feb. 10, 2020, 20 pages.

International Search Report and Written Opinion received for International PCT Application No. PCT/AU2018/051191 filed Nov. 2, 2018; Applicant: The Brain Protection Company PTY Ltd; dated Jan. 18, 2019, 20 pages.

International Search Report and Written Opinion received for International PCT Application No. PCT/AU2019/051101, filed Oct. 11, 2019; Applicant: The Brain Protection Company PTY Ltd; dated Dec. 19, 2019, 16 pages.

Sun et al., "Post-stroke cognitive impairment: epidemiology, mechanisms and management," Annals of Translational Medicine, 2014;2(8):80, published on Jul. 18, 2014, 16 pages.

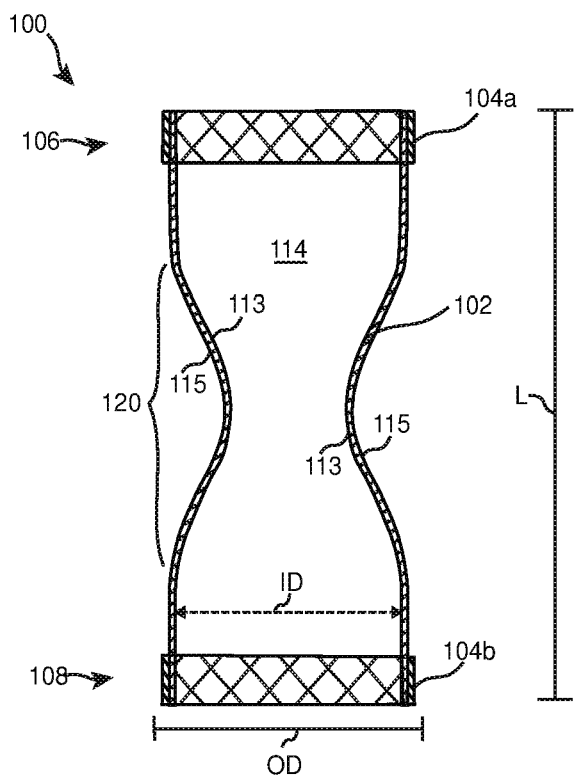
*Figure 2D*
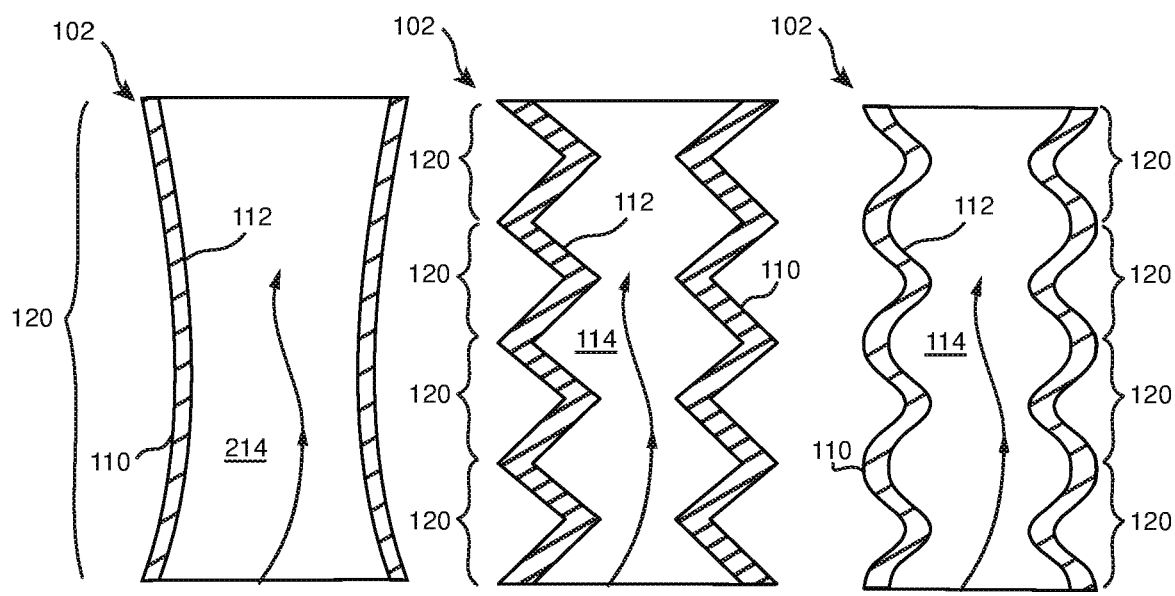
*Figure 2E*   *Figure 2F*   *Figure 2G*

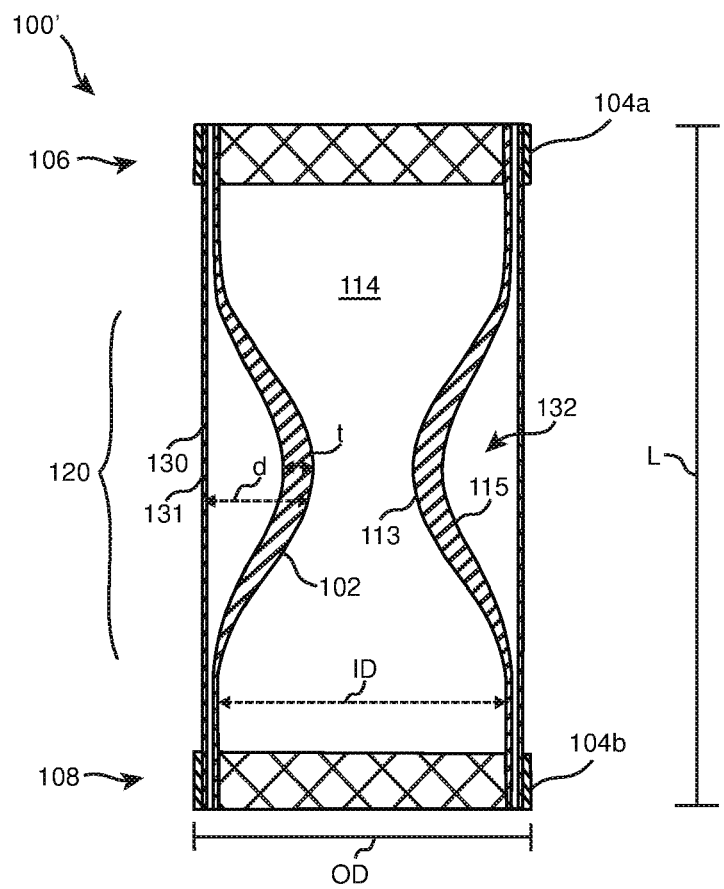
*Figure 3A*
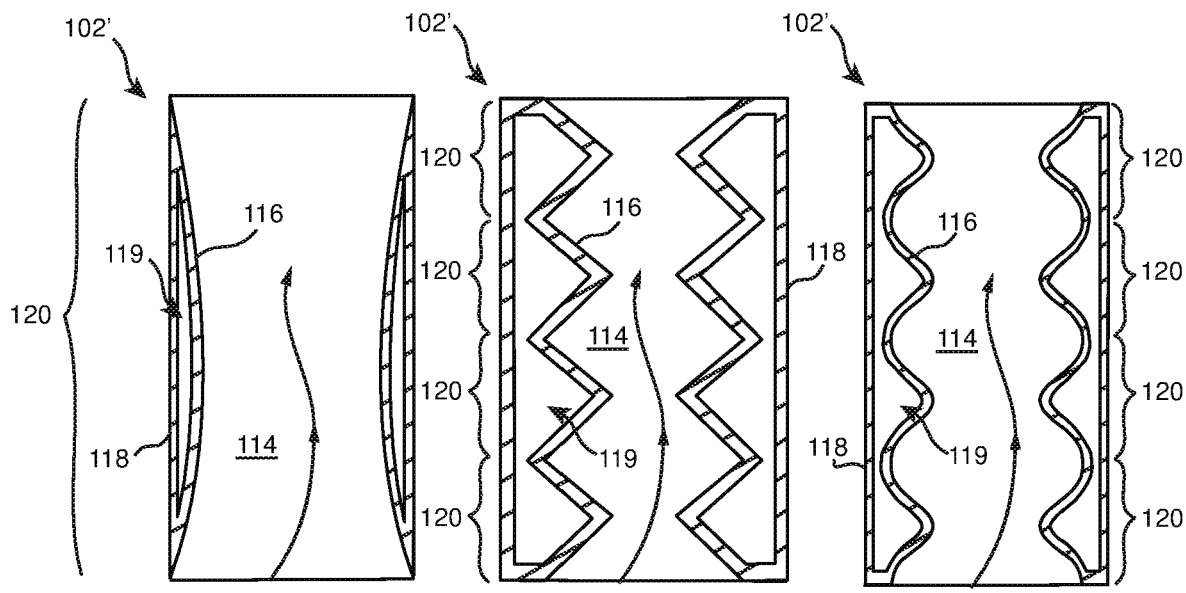
*Figure 3B*  *Figure 3C*  *Figure 3D*

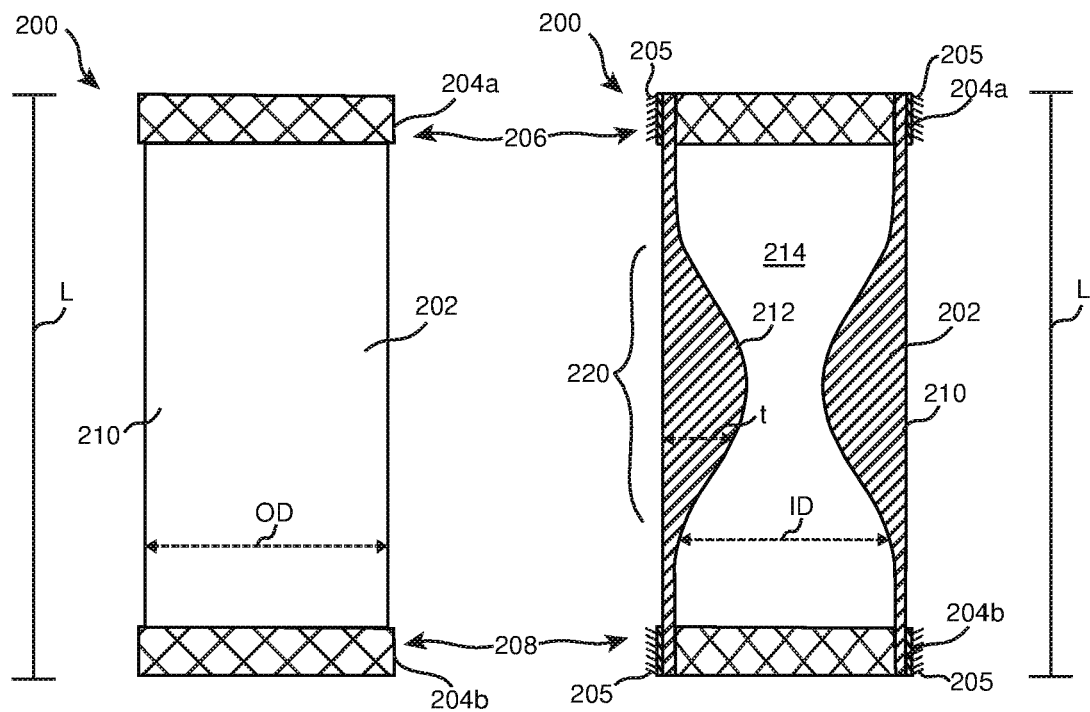
*Figure 4A*  *Figure 4B*
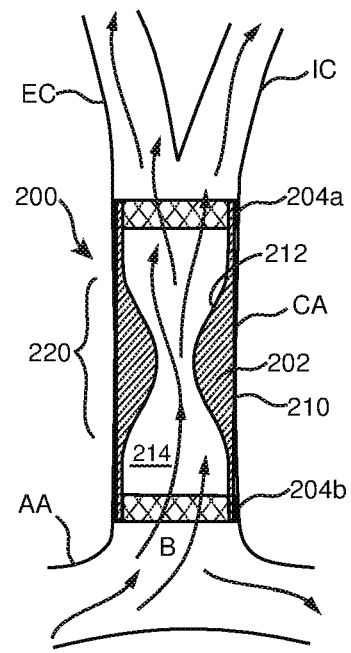
*Figure 4C*
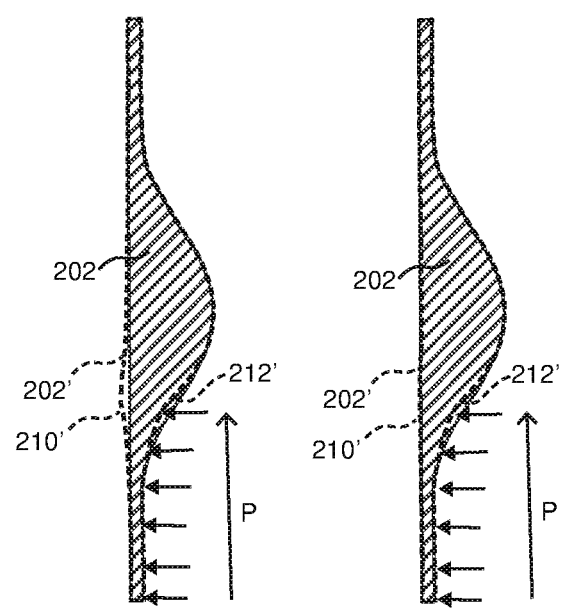
*Figure 4D*  *Figure 4E*

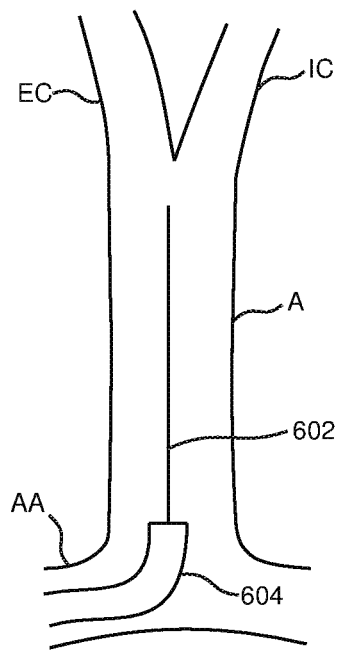
*Figure 8A*
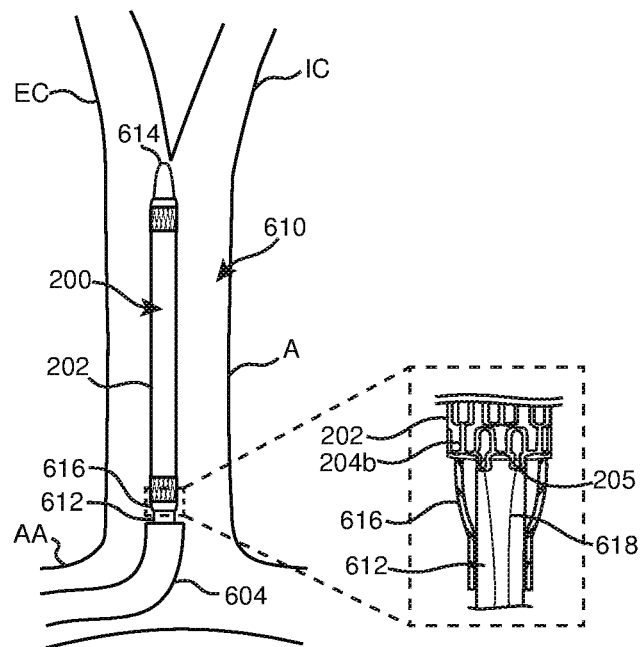
*Figure 8B*
*Figure 8C*
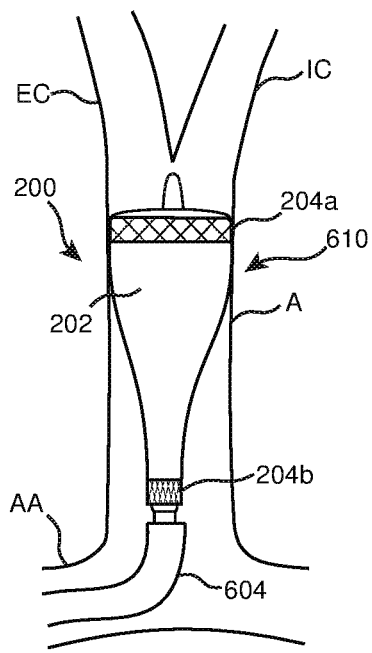
*Figure 8D*
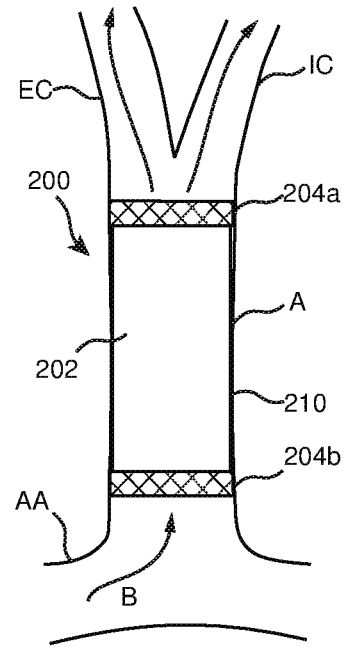
*Figure 8E*

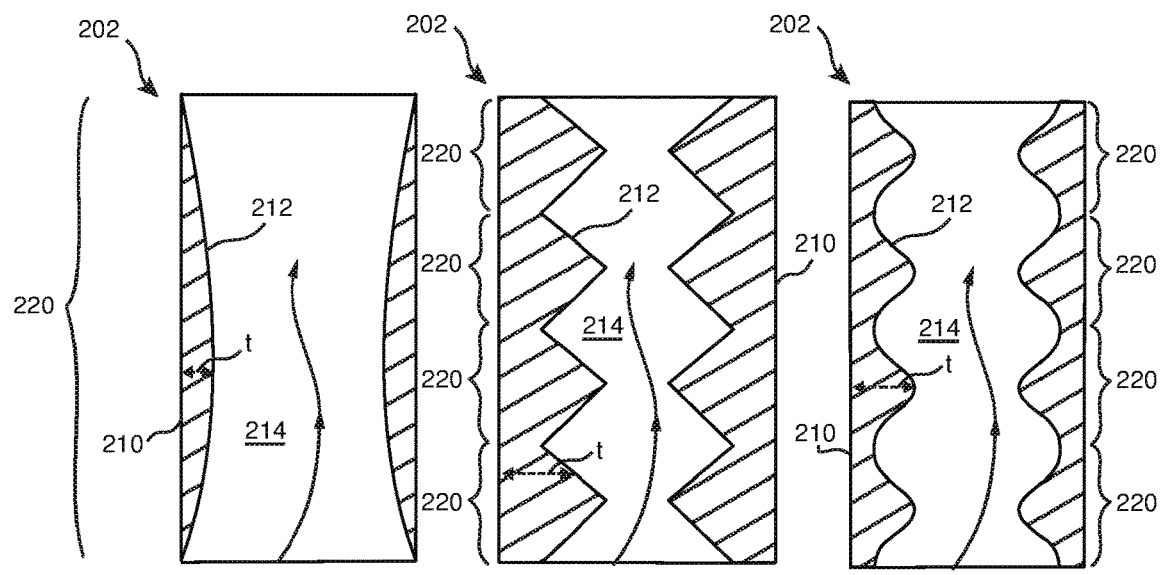
*Figure 9A*  *Figure 9B*  *Figure 9C*
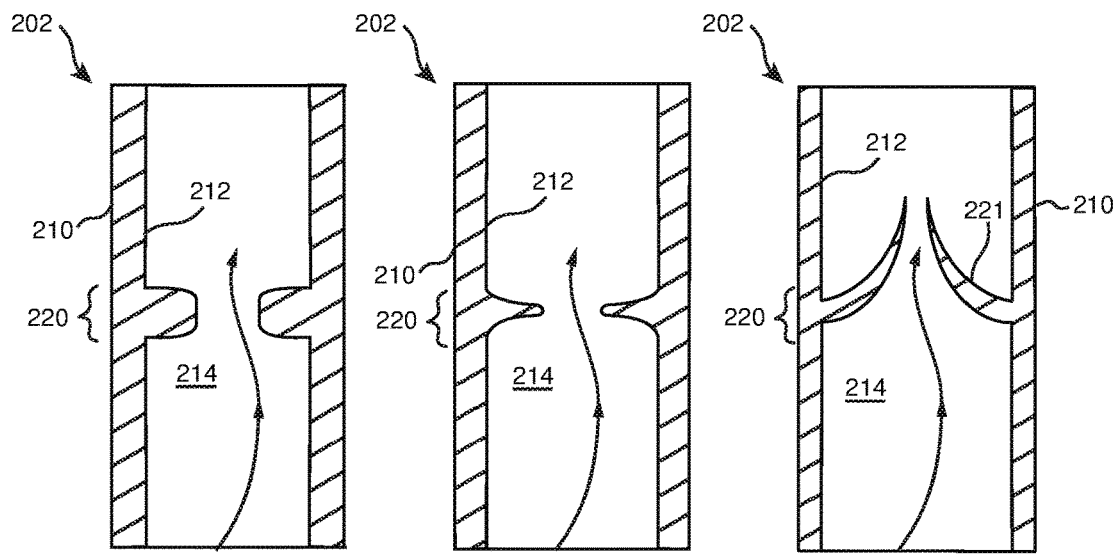
*Figure 9D*  *Figure 9E*  *Figure 9F*

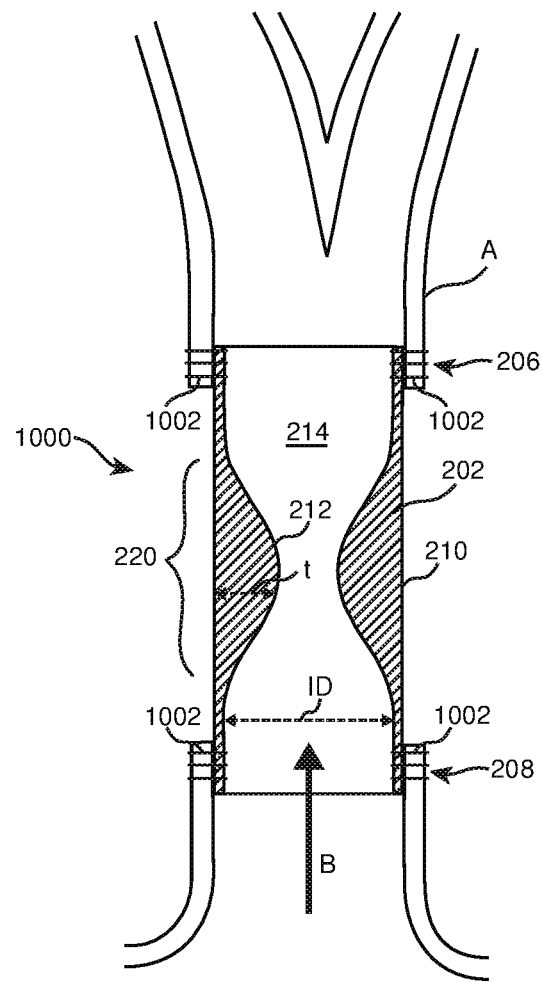
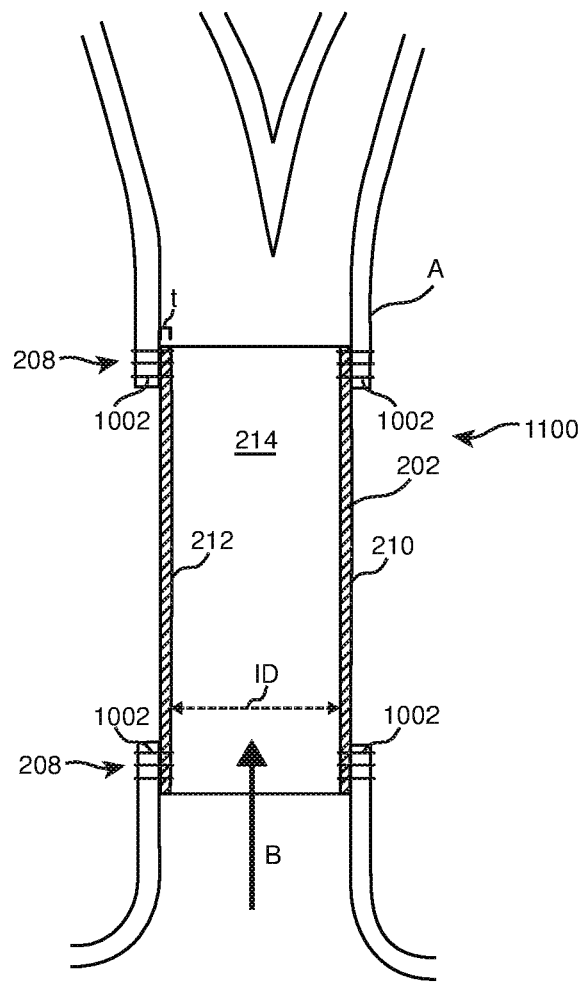
Figure 10                    Figure 11

IMPLANTABLE DAMPING DEVICES FOR TREATING DEMENTIA AND ASSOCIATED SYSTEMS AND METHODS OF USE

CROSS-REFERENCE TO RELATED APPLICATIONS

This application is a continuation of U.S. patent application Ser. No. 15/752,211, filed Feb. 12, 2018, which is a 35 U.S.C. § 371 U.S. National Phase application of International Patent Application No. PCT/AU2016/050734, filed Aug. 12, 2016, which claims priority to U.S. Provisional Application No. 62/341,575, filed on May 25, 2016, entitled "IMPLANTABLE DAMPING DEVICES FOR TREATING DEMENTIA AND ASSOCIATED SYSTEMS AND METHODS OF USE," and Australian Patent Application No. 2015903253, filed on Aug. 13, 2015, entitled "DEVICE AND METHOD FOR TREATING A BLOOD VESSEL," the contents of which are hereby incorporated by reference in their entireties.

TECHNICAL FIELD

The present technology relates to implantable damping devices for treating dementia and associated systems and methods of use. In particular, the present technology is directed to damping devices for treating an artery.

BACKGROUND

The heart supplies oxygenated blood to the body through a network of interconnected, branching arteries starting with the largest artery in the body—the aorta. As shown in the schematic view of the heart and selected arteries in FIG. 1A, the portion of the aorta closest to the heart is divided into three regions: the ascending aorta (where the aorta initially leaves the heart and extends in a superior direction), the aortic arch, and the descending aorta (where the aorta extends in an inferior direction). Three major arteries branch from the aorta along the aortic arch: the brachiocephalic artery, the left common carotid artery, and the left subclavian artery. The brachiocephalic artery extends away from the aortic arch and subsequently divides into the right common carotid artery, which supplies oxygenated blood to the head and neck, and the right subclavian artery, which predominantly supplies blood to the right arm. The left common carotid artery extends away from the aortic arch and supplies the head and neck. The left subclavian artery extends away from the aortic arch and predominantly supplies blood to the left arm. Each of the right common carotid artery and the left common carotid artery subsequently branches into separate internal and external carotid arteries.

During the systole stage of a heartbeat, contraction of the left ventricle forces blood into the ascending aorta that increases the pressure within the arteries (known as systolic blood pressure). The volume of blood ejected from the left ventricle creates a pressure wave—known as a pulse wave— that propagates through the arteries propelling the blood. The pulse wave causes the arteries to dilate, as shown schematically in FIG. 1B. When the left ventricle relaxes (the diastole stage of a heartbeat), the pressure within the arterial system decreases (known as diastolic blood pressure), which allows the arteries to contract.

The difference between the systolic blood pressure and the diastolic blood pressure is the "pulse pressure," which generally is determined by the magnitude of the contraction force generated by the heart, the heart rate, the peripheral vascular resistance, and diastolic "run-off" (e.g., the blood flowing down the pressure gradient from the arteries to the veins), amongst other factors. High flow organs, such as the brain, are particularly sensitive to excessive pressure and flow pulsatility. To ensure a relatively consistent flow rate to such sensitive organs, the walls of the arterial vessels expand and contract in response to the pressure wave to ab sorb some of the pulse wave energy. As the vasculature ages, however, the arterial walls lose elasticity, which causes an increase in pulse wave speed and wave reflection through the arterial vasculature. Arterial stiffening imp airs the ability of the carotid arteries and other large arteries to expand and dampen flow pulsatility, which results in an increase in systolic pressure and pulse pressure. Accordingly, as the arterial walls stiffen over time, the arteries transmit excessive force into the distal branches of the arterial vasculature.

Research suggests that consistently high systolic pressure, pulse pressure, and/or change in pressure over time (dP/dt) increases the risk of dementia, such as vascular dementia (e.g., an impaired supply of blood to the brain or bleeding within the brain). Without being bound by theory, it is believed that high pulse pressure can be the root cause or an exacerbating factor of vascular dementia and age-related dementia (e.g., Alzheimer's disease). As such, the progression of vascular dementia and age-related dementia (e.g., Alzheimer's disease) may also be affected by the loss of elasticity in the arterial walls and the resulting stress on the cerebral vessels. Alzheimer's Disease, for example, is generally associated with the presence of neuritic plaques and tangles in the brain. Recent studies suggest that increased pulse pressure, increased systolic pressure, and/or an increase in the rate of change of pressure (dP/dt) may, over time, cause microbleeds within the brain that may contribute to the neuritic plaques and tangles. Accordingly, there is a need for improved devices, systems, and methods for treating vascular and/or age-related dementia.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2D is a front cross-sectional view of another embodiment of a damping device in accordance with the present technology, shown in a deployed, relaxed state FIGS. 2E-2G are front cross-sectional views of several embodiments of damping members in accordance with the present technology, all shown in a deployed, relaxed state.

FIG. 3A is a front cross-sectional view of another embodiment of a damping device in accordance with the present technology shown in a deployed, relaxed state.

FIGS. 3B-3D are front cross-sectional views of several embodiments of damping members in accordance with the present technology, all shown in a deployed, relaxed state.

FIG. 4A is a front view of a damping device in accordance with another embodiment of the present technology, shown in a deployed, relaxed state.

FIG. 4B is a front cross-sectional view of the damping device shown in FIG. 4A.

FIG. 4C is a front cross-sectional view of the damping device shown in FIG. 4A, shown in a deployed state positioned within a blood vessel.

FIG. 4D is a front cross-sectional view of a portion of a damping member in accordance with the present technology showing deformation of the damping member (in dashed lines) in response to a pulse wave.

FIG. 4E is a front cross-sectional view of a portion of another damping member in accordance with the present technology showing deformation of the damping member (in dashed lines) in response to a pulse wave.

FIGS. 8A-8E illustrate a method of delivering a damping device to an artery in accordance with the present technology.

FIGS. 9A-9F are schematic cross-sectional views of several embodiments of damping members in accordance with the present technology.

FIGS. 10 and 11 are front cross-sectional views of embodiments of damping devices shown positioned at or near a resected blood vessel in accordance with the present technology.

DETAILED DESCRIPTION

The present technology is directed to implantable damping devices for treating or slowing the progression of dementia, which includes both vascular dementia and age-related dementia, and associated systems and methods of use. Some embodiments of the present technology, for example, are directed to damping devices including an anchoring member and a flexible, compliant damping member having an outer surface and an inner surface defining a lumen configured to direct blood flow. The inner surface is configured such that a cross-sectional dimension of the lumen varies. For example, the outer surface and the inner surface can be separated from each other by a distance that varies along the length of the damping member. The damping member can further include a first end portion, a second end portion opposite the first end portion, and a damping region between the first and second end portions. The distance between the outer surface and the inner surface of the damping member can be greater at the damping region than at either of the first or second end portions. When blood flows through the damping member during systole, the damping member absorbs a portion of the pulsatile energy of the blood to reduce the magnitude of the pulse pressure transmitted to a portion of the blood vessel distal to the damping device. Specific details of several embodiments of the technology are described below with reference to FIGS. 2A-19B.

With regard to the terms "distal" and "proximal" within this description, unless otherwise specified, the terms can reference a relative position of the portions of a damping device and/or an associated delivery device with reference to an operator, direction of blood flow through a vessel, and/or a location in the vasculature. For example, in referring to a delivery catheter suitable to deliver and position various damping devices described herein, "proximal" refers to a position closer to the operator of the device or an incision into the vasculature, and "distal" refers to a position that is more distant from the operator of the device or further from the incision along the vasculature (e.g., the end of the catheter).

As used herein, "artery" and "arteries that supply blood to the brain," include any arterial blood vessel (or portion thereof) that provides oxygenated blood to the brain. For example, "arteries" or "arteries that supply blood to the brain" can include the ascending aorta, the aortic arch, the brachiocephalic trunk, the right common carotid artery, the left common carotid artery, the left and right internal carotid arteries, the left and right external carotid arteries, and/or any branch and/or extension of any of the arterial vessels described above.

I. SELECTED INTRAVASCULAR EMBODIMENTS OF DAMPING DEVICES

Figure 1A:
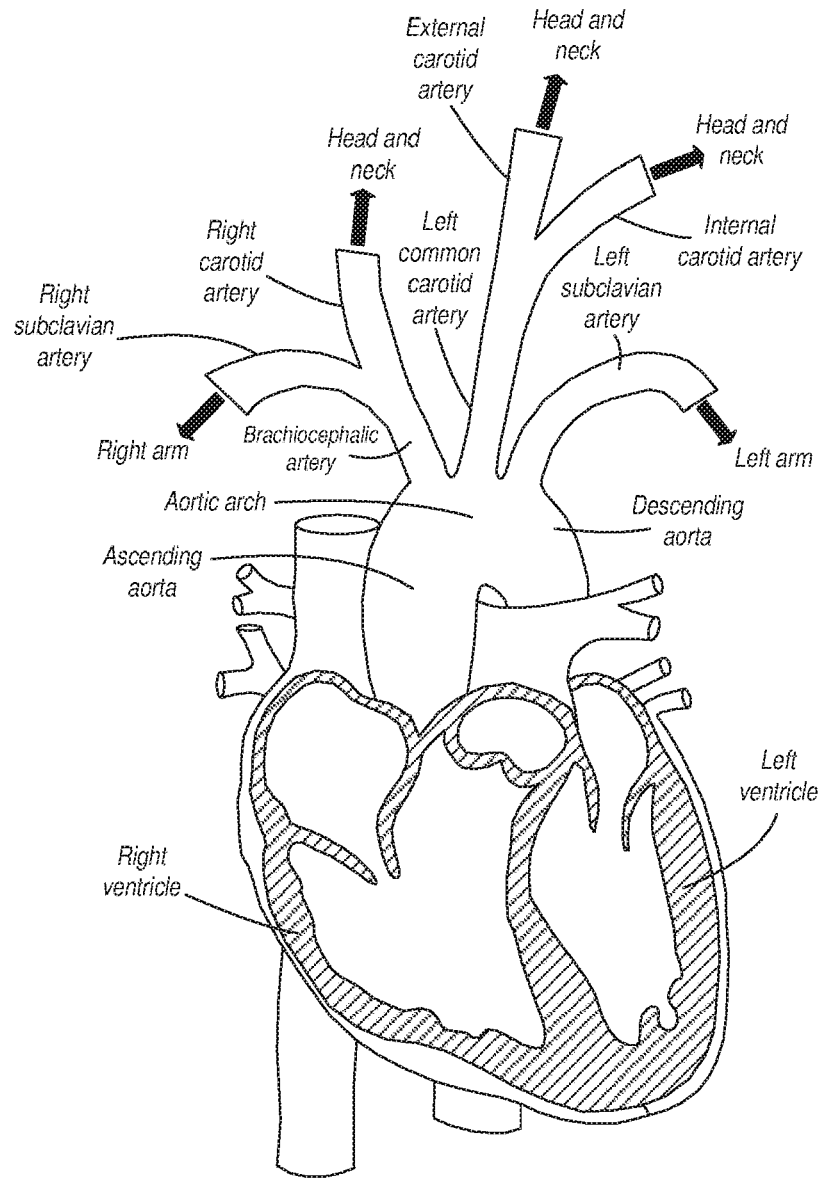
FIG. 1A is a schematic illustration of a human heart and a portion of the arterial system near the heart.
Figure 1B:
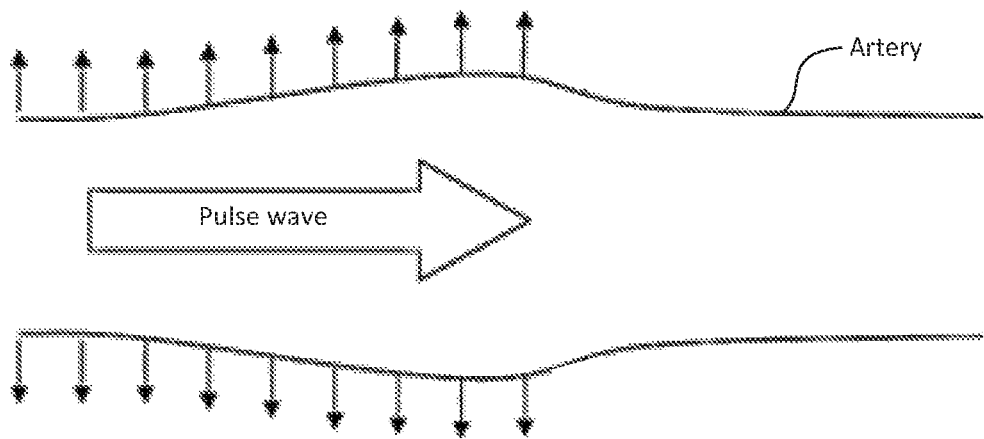
FIG. 1B is a schematic illustration of a pulse wave propagating along a blood vessel.
Figure 2A:
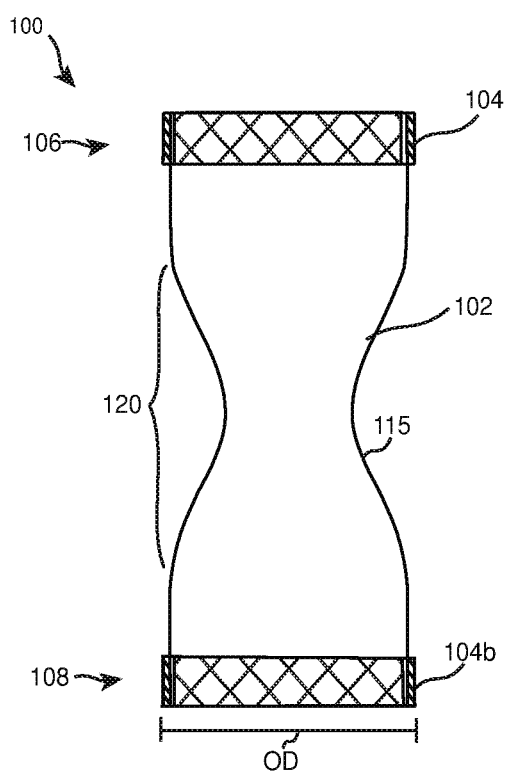
FIG. 2A is a front view of a damping device in accordance with the present technology, shown in a deployed, relaxed state.
Figure 2B:
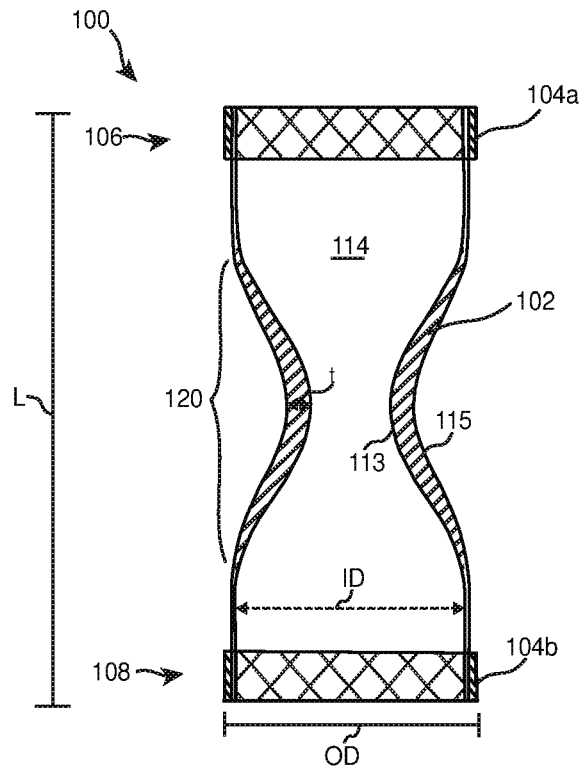
FIG. 2B is a front cross-sectional view of the damping device shown in FIG. 2A.
Figure 2C:
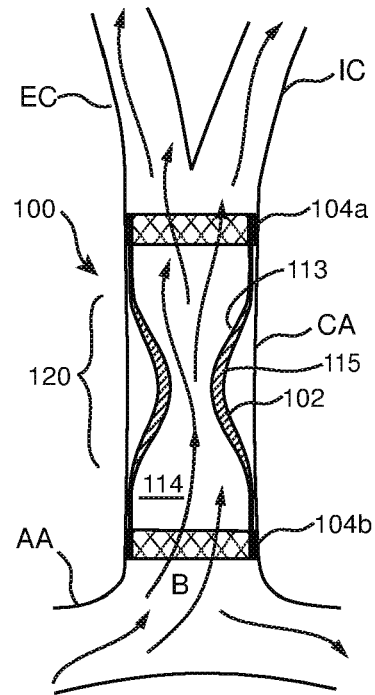
FIG. 2C is a front cross-sectional view of the damping device shown in FIG. 2A, shown in a deployed state positioned within a blood vessel.
Figure 5:
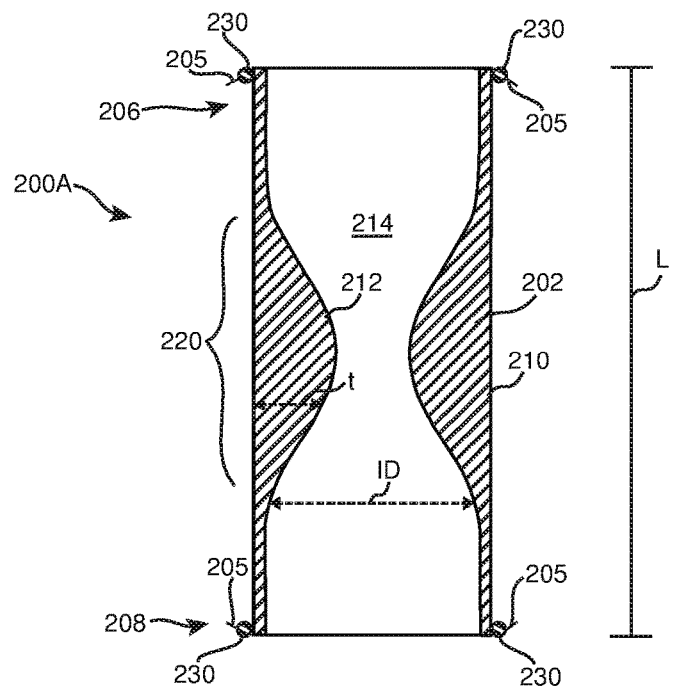
FIGS. 5-7 are front cross-sectional views of several embodiments of damping devices in accordance with the present technology.
Figures 6, 7:
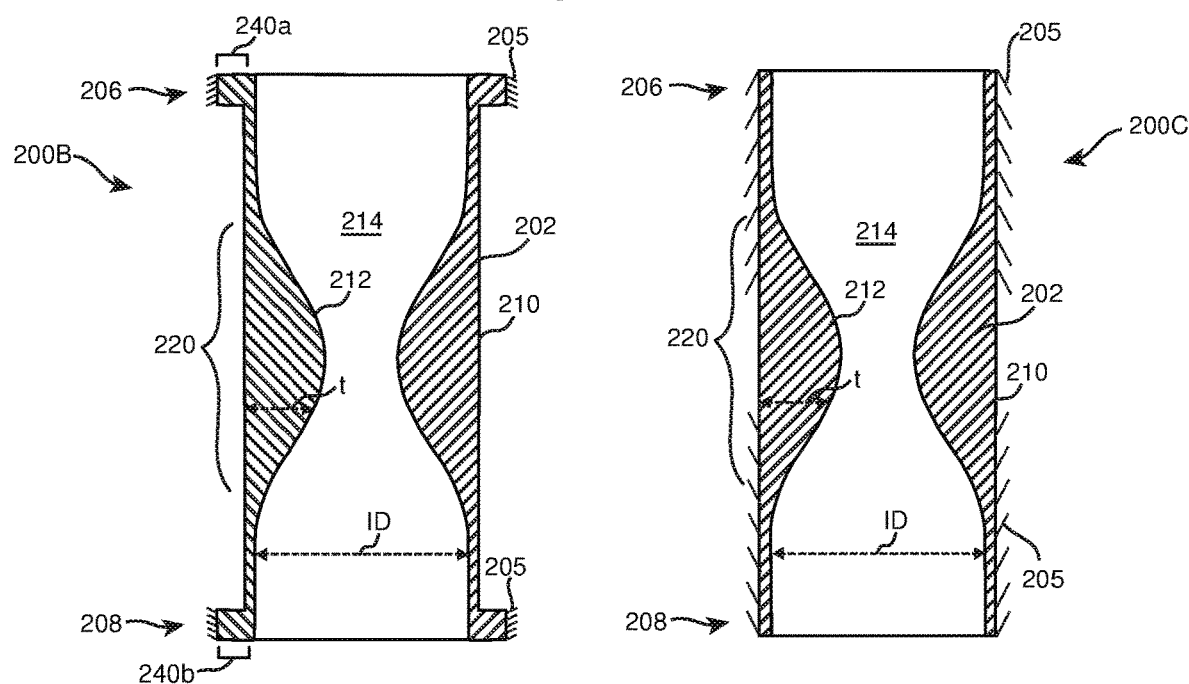

FIGS. 2A and 2B are a front view and a front cross-sectional view, respectively, of a damping device 100 configured in accordance with the present technology shown in an expanded or deployed state. FIG. 2C is a front view of the damping device 100 in a deployed state positioned in a carotid artery CA (e.g., the left or right carotid artery). Referring to FIGS. 2A-2C together, the damping device 100 includes a flexible, viscoelastic damping member 102 (e.g., a cushioning member) and anchoring members 104 (identified individually as first and second anchoring members 104a and 104b, respectively). The damping member 102 includes an undulating or hourglass-shaped sidewall having an outer surface 115 and an inner surface 113 (FIGS. 2B and 2C) that defines a lumen 114 configured to receive blood flow therethrough. The outer surface 115 is separated from the inner surface 113 by a distance t (FIG. 2B). The damping member 102 has a length L, a first end portion 106, and a second end portion 108 opposite the first end portion 106 along its length L, and a damping region 120 between the first end portion 106 and the second end portion 108. In the embodiment shown in FIGS. 2A-2C, the distance t between the outer and inner surfaces 115 and 113 varies along the length L of the damping member 102 when it is in a deployed, relaxed state. In some embodiments, the distance t between the outer and inner surfaces 115 and 113, on average, can be greater at the damping region 120 than at either of the first or second end portions 106, 108. In other embodiments, the damping member 102 can have other suitable shapes (for example, FIGS. 2E-2G), sizes, and/or configurations. For example, as shown in FIG. 2D, the distance t between the outer and inner surfaces 115 and 113 may be generally constant along the length of the damping member 102 and/or the damping region 120 when the damping member 102 is in a deployed, relaxed state.

The damping member 102 shown in FIGS. 2A-2C is a solid piece of material that is molded, extruded, or otherwise formed into the desired shape. The damping member 102 can be made of a biocompatible, compliant, viscoelastic material that is configured to deform in response to local fluid pressure in the artery. As the damping member 102 deforms, the damping member 102 absorbs a portion of the pulse pressure. The damping member 102, for example, can be made of a biocompatible synthetic elastomer, such as silicone rubber (VMQ), Tufel I and Tufel III elastomers (GE Advanced Materials, Pittsfield, MA), Sorbothane® (Sorbothane, Incorporated, Kent, OH), and others. The damping member 102 can be flexible and elastic such that the inner diameter ID of the damping member 102 at the damping region 120 increases as a systolic pressure wave propagates through the damping region 120. For example, a systolic pressure wave may push the inner surface 113 radially outwardly, thus forcing a portion of the outer surface 115 to also deform radially outwardly. Additionally, the damping member 102 can also optionally be compressible such that the distance t between the inner and outer surfaces 115 and 113 decreases to further open the inner diameter ID of the damping region 120 as the systolic pressure wave engages the damping region 120. For example, a systolic pressure wave may push the inner surface 113 radially outwardly while the contour of the outer surface 115 remains generally unaffected.

In the embodiment shown in FIGS. 2A-2C, the anchoring members 104a-104b individually comprise a generally cylindrical structure configured to expand from a low-profile state to a deployed state in apposition with the blood vessel wall. Each of the anchoring members 104a-b can be a stent formed from a laser cut metal, such as a superelastic material (e.g., Nitinol) or stainless steel. All or a portion of each of the anchoring members can include a radiopaque coating to improve visualization of the device during delivery, and/or the anchoring members may include one or more radiopaque markers. In other embodiments, the individual anchoring members 104a-104b can comprise a mesh or woven (e.g., a braid) construction in addition to or in place of a laser cut stent. For example, the individual anchoring members 104a-104b can include a tube or braided mesh formed from a plurality of flexible wires or filaments arranged in a diamond pattern or other configuration. In some embodiments, all or a portion of one or both of the anchoring members 104a-104b can be covered by a graft material (such as Dacron) to promote sealing with the vessel wall. Additionally, all or a portion of one or both anchoring members can include one or more biomaterials.

In the embodiment shown in FIGS. 2A-2B, the anchoring members 104a-104b are positioned around the damping member 102 at the first and second end portions 106, 108, respectively. As such, in this embodiment, the outer diameter OD of the damping member 102 is less than the inner diameter of the anchoring members 104a-104b. Also in the embodiment shown in FIGS. 2A-2B, the anchoring members 104a-104b are positioned around the damping member 102 only at the first and second end portions 106, 108, respectively. As such, in several embodiments of the present technology, the damping region 120 of the damping member 120 is not surrounded by a stent-like structure or braided material. In other embodiments, the anchoring members 104 and damping member 102 may have other suitable configurations. For example, the anchoring members 104a-104b may be positioned at other locations along the length L of the damping member 102, though not along the full length of the damping member 102. Also, in some embodiments, all or a portion of one or both anchoring members 104a-104b may be positioned radially outwardly of all or a portion of the damping member 102. Although the damping device 100 shown in FIGS. 2A-2B includes two anchoring members 104a-104b, in other embodiments the damping device 100 can have more or fewer anchoring members (e.g., one anchoring member, three anchoring members, four anchoring members, etc.).

In some embodiments, a biocompatible gel or liquid may be located between the wall of the artery A and the outer surface 115 of the damping member 102 to prevent the ingression of blood into the void defined between the first anchoring member 104a, the second anchoring member 104b, the damping member 102, and the inner wall of the artery CA. Alternatively, air or another gas may be located between the internal wall of the carotid artery CA and the damping member 102 to prevent the ingression of blood into the void.

FIG. 3A is a front cross-sectional view of another embodiment of a damping device 100' in accordance with the present technology. The embodiment of the damping device 100' shown in FIG. 3A is similar to the embodiment of the damping device 100 shown in FIGS. 2A-2C, and like reference numbers refer to like components in FIGS. 2A-2C and FIG. 3A. As shown in FIG. 3A, the damping device 100' includes an inner damping member 102 and an outer layer 130 surrounding the damping member 102. The outer layer 130 has an outer surface 131 and, in the embodiment shown in FIG. 3A, the first and second anchoring members 104a-b are attached to the outer surface 131. At least along the damping region 120, the outer layer 130 is spaced apart from the outer surface 115 of the damping member 102 to form a chamber 132. The chamber 132 can be at least partially filled with a fluid, such as a gas, liquid, or gel. The device 100' has a length L and a distanced between the outer surface 131 of the outer layer 130 and the inner surface 113 of the damping member 102. Along the damping region 120, the distance d between the outer and inner surfaces 131 and 113 increases then decreases in a radial direction when the damping member 102 is in a deployed, relaxed state. On average, the distanced between the outer surface 131 and the inner surface 113 of the damping member 102 is greater at the damping region 120 than at either of the first or second end portions 106,108. As a result, the diameter ID of the lumen 114 varies along the length L. For example, the outer surface 131 and/or the outer layer 130 can be generally cylindrical in an unbiased state, and the inner surface 113 and/or the damping member 102 can have an undulating or hourglass shape. In other embodiments, the outer surface 131 and/or the outer layer 130 can be other suitable shapes, and the inner surface 113 and/or the damping member 102 can be other suitable shapes (FIGS. 3B-3D).

In some embodiments, instead of the damping device 100' having a separate outer layer 130, the damping member 102 can be molded, formed, or otherwise extruded to enclose a cavity. For example, as shown in FIGS. 3B-3D, the damping member 102' can include an inner layer 116, an outer layer 118, and a cavity 119 therebetween. The cavity 119 can be at least partially filled with a fluid, such as a gas, liquid, or gel.

FIGS. 4A and 4B are a front view and a front cross-sectional view, respectively, of another embodiment of a damping device 200 configured in accordance with the present technology shown in an expanded or deployed state. FIG. 4C is a front cross-sectional view of the damping device 200 in a deployed state positioned in a carotid artery (e.g., the left or right carotid artery). Referring to FIGS. 4A-4C together, the damping device 200 includes a flexible, viscoelastic damping member 202 (e.g., a cushioning member) and anchoring members 204 (identified individually as first and second anchoring members 204a-204b, respectively). As shown in FIGS. 4B and 4C, the damping member 202 includes a generally tubular sidewall having a cylindrical outer surface 210 and an inner surface 212 that defines a lumen 214 configured to receive blood flow therethrough. The outer surface 210 is separated from the inner surface 212 by a distance t (FIG. 4B). The damping member 202 has a length L, a first end portion 206, and a second end portion 208 opposite the first end portion 206 along its length L, and a damping region 220 between the first end portion 206 and the second end portion 208. Along the damping region 220, the distance t between the outer and inner surfaces 210 and 212 increases then decreases in a radial direction when the damping member 202 is in a deployed, relaxed state. On average, the distance t between the outer and inner surfaces 210 and 212 of the damping member 202 is greater at the damping region 220 than at either of the first or second end portions 206, 208. As a result, the inner diameter ID of the damping member 202 varies along its length L relative to the outer diameter OD of the damping member 202. For example, the outer surface 210 can be generally cylindrical in an unbiased state, and the inner surface 212 can have an undulating or hourglass shape. As described in greater detail below with respect to FIGS. 9A-9F, the damping member 202 can have other suitable shapes, sizes, and/or configurations.

The damping member 202 shown in FIGS. 4A-4C is a solid piece of material that is molded, extruded, or otherwise formed into the desired shape. The damping member 202 can be made of a biocompatible, compliant, viscoelastic material that is configured to deform in response to local fluid pressure in the artery. As the damping member 202 deforms, the damping member 202 absorbs a portion of the pulse pressure. The damping member 202, for example, can be made of a biocompatible synthetic elastomer, such as silicone rubber (VMQ), Tufel I and Tufel III elastomers (GE Advanced Materials, Pittsfield, MA), Sorbothane® (Sorbothane, Incorporated, Kent, OH), and others. The damping member 202 can be flexible and elastic such that the inner diameter ID of the damping member 202 at the damping region 220 increases as a systolic pressure wave P (FIG. 4D) propagates through the damping region 220. For example, as shown schematically in the isolated, cross-sectional view of a portion of a damping member 202 before and during deformation (damping member 202', shown in dashed lines) in FIG. 4D, the systolic pressure wave P may push the inner surface 212' radially outwardly, thus forcing a portion of the outer surface 210' to also deform radially outwardly. Additionally, the damping member 202 can also optionally be compressible such that the distance t between the inner and outer surfaces 210 and 212 decreases to further open the inner diameter ID of the damping region 220 as the systolic pressure wave P engages the damping region 220. For example, as shown schematically in the isolated, cross-sectional view of a portion of a damping member 202 before and during deformation (damping member 202', shown in dashed lines) in FIG. 4E, the systolic pressure wave P may push the inner surface 212' radially outwardly while the contour of the outer surface 210' remains generally unaffected.

In the embodiment shown in FIGS. 4A-4C, the anchoring members 204a-204b individually comprise a generally cylindrical structure configured to expand from a low-profile state to a deployed state in apposition with the blood vessel wall. Each of the anchoring members 204a-b can be a stent formed from a laser cut metal, such as a superelastic material (e.g., Nitinol) or stainless steel. All or a portion of each of the anchoring members can include a radiopaque coating to improve visualization of the device during delivery, and/or the anchoring members may include one or more radiopaque markers. In other embodiments, the individual anchoring members 204a-204b can comprise a mesh or woven (e.g., a braid) construction in addition to or in place of a laser cut stent. For example, the individual anchoring members 204a-204b can include a tube or braided mesh formed from a plurality of flexible wires or filaments arranged in a diamond pattern or other configuration. In some embodiments, all or a portion of one or both of the anchoring members 204a-204b can be covered by a graft material (such as Dacron) to promote sealing with the vessel wall.

In the embodiment shown in FIGS. 4A-4B, the anchoring members 204a-204b are positioned around the damping member 202 at the first and second end portions 206, 208, respectively. As such, in this embodiment, the outer diameter OD (FIG. 4A) of the damping member 202 is less than the inner diameter of the anchoring members 204a-204b. Also in the embodiment shown in FIGS. 4A-4B, the anchoring members 204a-204b are positioned around the damping member 202 only at the first and second end portions 206, 208, respectively. As such, in several embodiments of the present technology, the damping region 220 of the damping member 220 is not surrounded by a stent-like structure or braided material. In other embodiments, the anchoring members 204a-204b and damping member 202 may have other suitable configurations. For example, the anchoring members 204a-204b may be positioned at other locations along the length L of the damping member 202, though not along the full length of the damping member 202. Also, in some embodiments, all or a portion of one or both anchoring members 204a-204b may be positioned radially outwardly of all or a portion of the damping member 202. Although the damping device 200 shown in FIGS. 4A-4B includes two anchoring members 204a-204b, in other embodiments the damping device 200 can have more or fewer anchoring members (e.g., one anchoring member, three anchoring members, four anchoring members, etc.).

In some embodiments, one or both of the anchoring members 204a-204b can optionally include one or more fixation elements 205 (FIG. 4B) configured to engage the blood vessel wall. The fixation elements 205 can include, for example, one or more hooks or barbs that, in the deployed state, extend outwardly away from the corresponding frames of the anchoring member 204a-204b to penetrate the vessel wall at the treatment site. In these and other embodiments, one or more of the fixation elements can be atraumatic. Additionally, referring to the damping device 200A shown in FIG. 5, in certain embodiments the damping device 200 may not include a stent-type or braid type anchoring member, but rather the frame of the anchoring members 204 can be one or more expandable rings 230. For example, in some embodiments the damping device 200 can include two rings 230, each attached to a respective end portion 206 and 208, and the plurality of fixation elements 205 can extend outwardly from the rings 230. In still other embodiments, such as the damping device 200B shown in FIG. 6, the anchoring members 204 can be integral portions of the end portions 206, 208, such as thick wall portions 240a-b of the damping member 202 that extend radially outward from the outer wall of the damping region 220, instead of separate metal or polymeric components. In this embodiment, the fixation elements 205 can extend outwardly from integral anchoring members 240a-b at the first and second end portions 206, 208 of the damping member 202. When the damping device 200 is in a deployed state, the fixation elements 205 extend outwardly away from the outer surface of the damping member 202 to engage vessel wall tissue. In yet other embodiments, the fixation elements 205 can extend outwardly from the outer surface 210 of the damping member 202, as shown in the damping device 200C of FIG. 7.

FIGS. 8A-8E illustrate a method for positioning a damping device of the present disclosure at a treatment location within an artery A (such as the left and/or right common carotid artery CA). Although FIGS. 8B-8E depict the damping device 200 shown in FIGS. 4A and 4B, the methods and systems described with respect to FIGS. 8A-8E can be utilized for any of the damping devices 100, 100', 200, 200A, 200B, and 200C described with respect to FIGS. 2A-7 and FIGS. 9A-9F.

As shown in FIG. 8A, a guidewire 602 may first be advanced intravascularly to the treatment site from an access site, such as a femoral or a radial artery. A guide catheter 604 may then be advanced along the guidewire 602 until at least a distal portion of the guide catheter 604 is positioned at the treatment site. In these and other embodiments, a rapid-exchange technique may be utilized. In some embodiments, the guide catheter 604 may have a pre-shaped or steerable distal end portion to direct the guide catheter 604 through one or more bends in the vasculature. For example, the guide catheter 604 shown in FIGS. 8A-8E has a curved distal end portion configured to navigate through the ascending aorta AA and preferentially bend or flex at the left and/or right common carotid artery A to direct the guide catheter 604 into the artery A.

Image guidance, e.g., computed tomography (CT), fluoroscopy, angiography, intravascular ultrasound (IVUS), optical coherence tomography (OCT), or another suitable guidance modality, or combinations thereof, may be used to aid the clinician's positioning and manipulation of the damping device 200. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the damping device 200. Further, in some embodiments, image guidance components (e.g., IVUS, OCT) may be integrated with the delivery catheter and/or run in parallel with the delivery catheter to provide image guidance during positioning of the damping device 200.

Once the guide catheter 604 is positioned at the treatment site, the guidewire 602 may be withdrawn. As shown in FIGS. 8B and 8C, a delivery assembly 610 carrying the damping device 200 may then be advanced distally through the guide catheter 604 to the treatment site. In some embodiments, the delivery assembly 610 includes an elongated shaft 612 having an atraumatic distal tip 614 (FIG. 8B) and an expandable member 616 (e.g., an inflatable balloon, an expandable cage, etc.) positioned around a distal portion of the elongated shaft 612. The damping device 200 can be positioned around the expandable member 616. As shown in FIG. 8D, expansion or inflation of the expandable member 616 forces at least a portion of the damping device 200 radially outwardly into contact with the arterial wall. In some embodiments, the delivery assembly 610 can include a distal expandable member for deploying a distal portion of the damping device 200, and a proximal expandable member for deploying a proximal portion of the damping device 200. In other embodiments, the entire length of the damping device 200 may be expanded at the same time by deploying one or more expandable members.

In some procedures the clinician may want to stretch or elongate the damping device 200 before deploying the proximal second anchoring member 204b against the arterial wall. To address this need, the delivery assembly 610 and/or damping device 200 can optionally include a tensioning mechanism for pulling or providing a tensile stress on the second anchoring member 204b, thereby increasing the length of the damping member 202 and/or a distance between the first and second and anchoring members 204a, 204b. For example, as shown in FIG. 8C, the second anchoring member 204b can include one or more coupling portions 205 (e.g., one or more eyelets extending proximally from the anchoring frame) and one or more coupling members 618 (e.g., a suture, a thread, a filament, a tether, etc.) extending between the second anchoring member 204b and a proximal portion (not shown) of the delivery assembly 610 (e.g., a handle). The coupling members 618 are configured to releasably engage the coupling portions 205 to mechanically couple the second anchoring member 204b to a proximal portion of the delivery assembly 610. A clinician can apply a tensile force to the coupling member 618 to elongate the damping device 200 and/or damping member 202 and adjust the longitudinal position of the second anchoring member 204b. Once the second anchoring member 204b is positioned at a desired longitudinal position relative to the first anchoring member 204a and/or the local anatomy, the second anchoring member 204b can be expanded into contact with the arterial wall (e.g., via deployment of one or more expandable members). Before, during, and/or after expansion of the second anchoring member 204b, the coupling member(s) 618 may be disengaged from the second anchoring member 204b. For example, in some embodiments, the operator can force the coupling members 618 to break along their lengths by applying a tensile force that is less than a force that would be required to dislodge one or both of the first and second anchoring members 204a, 204b. Once disengaged from the second anchoring member 204b and/or the damping device 200, the coupling member(s) 618 can then be withdrawn from the treatment site through the guide catheter 604.

In other embodiments, other tensioning mechanisms may be utilized. For example, in some embodiments, the damping device 200 includes a releasable clasp, ring, or hook which is selectively releasable by the operator. The clasp, ring or hook may be any type that permits securement of the thread to the second anchoring member 204b, and which can be selectively opened or released to disengage the thread from the second anchoring member 204b. The releasing can be controlled by the clinician from an extracorporeal location. Although the tensioning mechanism is described herein with respect to the second anchoring member 204b, it will be appreciated that other portions of the damping device 200 and/or the delivery assembly 610 (such as the first anchoring member 204a) can be coupled to a tensioning mechanism.

In certain embodiments, the damping member 202 and/or individual anchoring members 204a, 204b may be self-expanding. For example, the delivery assembly 610 can include a delivery sheath (not shown) that surrounds and radially constrains the damping device 200 during delivery to the treatment site. Upon reaching the treatment site, the delivery sheath may be at least partially withdrawn or retracted to allow the damping member 202 and/or the individual anchoring members 204a, 204b to expand. In some embodiments, expansion of the anchoring members 204 may drive expansion of the damping member 202. For example, the anchoring members 204 may be fixedly attached to the damping member 202, and expansion of one or both anchoring 204 pulls or pushes (depending on the relative positioning of the damping member 202 and anchoring members 204) the damping member 202 radially outwardly.

As best shown in FIG. 8C, once the damping device 200 is positioned at the treatment site (e.g., in a left or right common carotid artery), oxygenated blood ejected from the left ventricle flows through the lumen 214 of the damping member 202. As the blood contacts the damping region 220 of the damping member 202, the damping region 220 deforms to absorb a portion of the pulsatile energy of the blood, which reduces a magnitude of a pulse pressure transmitted to the portions of the artery distal to the damping device 200 (such as the more-sensitive cerebral arteries). The damping region 202 acts a pressure limiter that distributes the pressure of the systolic phase of the cardiac cycle more evenly downstream from the damping device 200 without unduly compromising the volume of blood flow through the damping device 200. Accordingly, the damping device 200 reduces the pulsatile stress on downstream portions of the arterial network to prevent or at least partially reduce the manifestations of vascular dementia and/or age-related dementia.

In some procedures, it may be beneficial to deliver multiple damping devices 200 to multiple arterial locations. For example, after deploying a first damping device 200 at a first arterial location (e.g., the left or right common carotid artery, an internal or external carotid artery, the ascending aorta, etc.), the clinician may then position and deploy a second damping device 200 at a second arterial location different than the first arterial location (e.g., the left or right common carotid artery, an internal or external carotid artery, the ascending aorta etc.). In a particular application, a first damping device is deployed in the left common carotid artery and the second damping device is deployed in the right common carotid artery. In other embodiments, two or more damping devices 200 may be delivered simultaneously.

In some embodiments, an additional stent of larger diameter may be placed within the vessel prior to deployment of the damping device 200 to expand the diameter of the vessel in preparation for the device. Subsequently, the damping device 200 can be deployed within the larger stent. This may assist to reduce impact on the residual diameter of the vessel, and thereby reduce impact on blood flow rate.

FIGS. 9A-9F are schematic cross-sectional views of several embodiments of damping members in accordance with the present technology. Like reference numbers refer to similar or identical components in FIGS. 2A-9F. In the embodiment shown in FIG. 9A, the inner surface 212 of the damping member 202 is curved along its entire length. The distance between the outer surface 210 and the inner surface 212 gradually increases then decreases in a distal direction. As such, the damping region 220 extends the entire length of the damping member 202. FIGS. 9B and 9C illustrate embodiments of the damping member 202 in which the inner surface 212 has a series of damping regions 220 defined by undulations in the inner surface 212. In these embodiments, the distance t increases, then decreases, then increases, then decreases, etc. in a distal direction. In FIG. 9B, the damping regions 220 are generally linear, while in FIG. 9C, the damping regions 220 are generally curved. FIGS. 9D-9E illustrate embodiments of damping members 202 having damping regions 220 comprising an annular ring projecting radially inwardly into the lumen 214. One or more portions of the annular ring may flex in a longitudinal direction in response to blood flow. As shown in FIG. 9F, in some embodiments the damping member 220 can comprise two or more opposing leaflets 221.

II. SELECTED RESECTION EMBODIMENTS OF DAMPING DEVICES

FIGS. 10 and 11 are schematic cross-sectional views of several embodiments of damping devices in accordance with the present technology. Like reference numbers refer to similar or identical components in FIGS. 2A-15. FIG. 10, for example, shows a damping device 1000 comprising only the damping member 202. A portion of the arterial wall A may be resected, and the damping member 202 may be coupled to the open ends of the resected artery (e.g., via sutures 1002) such that the damping member 202 spans the resected portion of the artery A. In some embodiments, the damping member 202 may have a generally cylindrical shape with a constant wall thickness, as shown in FIG. 11. In such embodiments, an inner diameter ID of the damping member 202 may be generally constant along the length of the damping member 202. In operation, the damping devices 1000 and 1100 shown in FIGS. 10 and 11 are highly flexible, elastic members that expand radially outward as the systolic pressure wave passes through the damping devices 1000 and 1100. Since the resected portions of the arterial wall A cannot limit the expansion of the damping devices 1000 and 1100, these devices can expand more than the native arterial wall A to absorb more energy from the blood flow.

III. SELECTED ADDITIONAL EMBODIMENTS OF DAMPING DEVICES

Figure 12A:
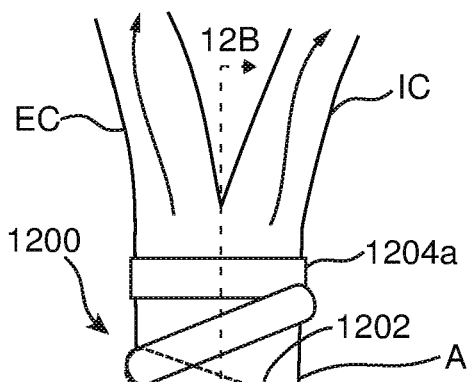
FIG. 12A is a front view of a helical damping device in accordance with the present technology, shown positioned around a blood vessel in a deployed, relaxed state.

FIGS. 12A-19B illustrate additional embodiments of damping devices configured in accordance with the present technology. For example, FIG. 12A shows a damping device 1200 comprising a damping member 1202 coupled to anchoring members 1204a and 1204b at its proximal and distal end portions. The damping member 1202 comprises a strand 1203 having a pre-set helical configuration such that, in a deployed state, the strand 1203 forms a generally tubular structure defining a lumen extending therethrough. The tubular structure has an inner surface 1209 (FIG. 12B) and an outer surface 1211. The strand 1203 may be formed of any suitable biocompatible material such as one or more elastic polymers that are configured to stretch in response to the radially outward forces exerted by the pulse wave on the helical strand. In some embodiments, the strand 1203 may additionally or alternatively include one or more metals such as stainless steel and/or a superelastic and/or shape memory alloy, such as Nitinol. In a particular embodiment, the damping member 1202 may be fabricated from a recombinant human protein such as tropo-elastin or elastin.

The anchoring members 1204a and 1204b can be generally similar to the anchoring members 104a and 104b described with respect to FIGS. 2A-2C. In some embodiments, the damping device 1200 includes more or fewer than two anchoring members 1204 (one anchoring member, three anchoring members, etc.). In a particular embodiment, the damping device 1200 does not include anchoring members 1204.

In the deployed state, the damping member 1202 is configured to be wrapped along the circumference of an artery that supplies blood to the brain. For example, in the embodiment shown in FIG. 12A, the damping member 1202 is configured to be positioned around the exterior of the artery A such that the inner surface 1209 of the damping member 1202 contacts an outer surface of the artery A (see FIG. 12B). In other embodiments (not shown), the damping member 1202 is configured to be positioned around the lumen of the artery such that the outer surface 1211 of the damping member 1202 contacts an inner surface of the arterial wall.

Figure 12B:
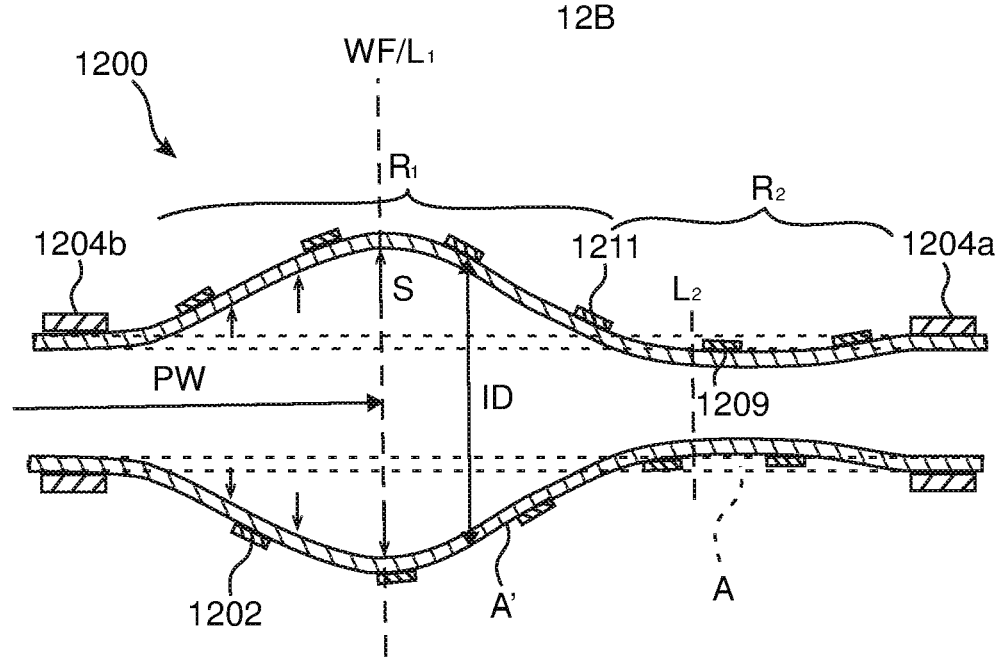
FIG. 12B is a cross-sectional view of the damping device of FIG. 12A (taken along line 12B-12B in FIG. 12A), shown positioned around the blood vessel as a pulse pressure wave travels through the vessel.

FIG. 12B is a cross-sectional side view of the damping device 1200 during transmission of a pulse wave PW through the portion of the artery A surrounded by the damping device 1200. In FIG. 12B, the dashed lines A represent the artery during diastole, or when the artery is relaxed. The solid line A' represents the artery in response to a pulse wave PW traveling through the artery during systole. As shown in FIG. 12B, as the wave front WF (or leading edge of the pulse wave PW) travels through the artery, the wavefront dilates the artery A at an axial location $L_1$ corresponding to the wavefront WF. The wavefront WF pushes the arterial wall radially outwardly against the coil, thereby radially expanding the portion $R_1$ of the coil axially aligned with the wave front WF. For example, in those embodiments where the strand 1203 is made of a stretchable material, such as an elastic polymer, the coil stretches along the portion $R_1$ to expand and accommodate the pulse wave, thereby absorbing some of the energy transmitted with the pulse wave and reducing the stress on the arterial wall. In any of the above embodiments, the portions of the coil distal or proximal the wave-affected region are forced to contract ($R_2$), thereby causing the artery to narrow relative to its relaxed diameter. This narrowing of the artery creates a temporary impedance to the pulse wave which absorbs some of the energy. Once the pulse wave has passed, the arterial wall returns to its relaxed state.

Figure 13:
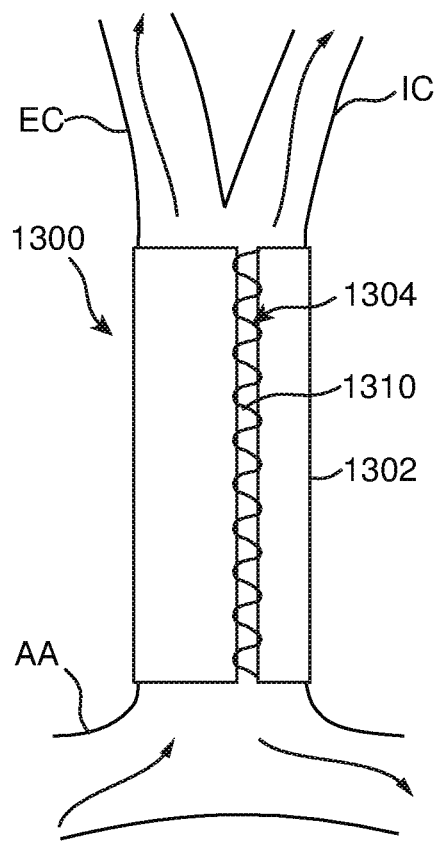
FIGS. 13 and 14 show different embodiments of a wrapped damping device, each shown positioned around a blood vessel in accordance with the present technology.

FIG. 13 illustrates another embodiment of a damping device 1300 in accordance with the present technology. As shown in FIG. 13, the damping device 1300 can include a damping member 1302 defined by an extravascular wrap. The damping member 1302 may be fabricated from a generally rectangular portion of a suitable bio-compatible and elastically deformable material which is configured to be wrapped around the blood vessel. Alternatively, the damping member 1302 may be initially provided having a cylindrical configuration including a longitudinal slit 1304 for receiving the vessel. The damping member 1302 may be fabricated from a synthetic such as an elastic polymer, a shape memory and/or superelastic material such as Nitinol (nickel titanium), a recombinant human protein such as tropo-elastin or elastin, and other suitable materials. As shown in FIG. 13, the damping member 1302 is configured to be secured around an artery (e.g., a carotid artery) between the aortic arch and the junction where the left common carotid artery divides into the internal (IC) and external (EC) carotid arteries. It will be appreciated by those skilled in the art that the damping member 1302 may alternatively or additionally be deployed around the brachiocephalic trunk (not shown) or the right common carotid artery (not shown), or any distal branch of the aforementioned arteries, or any proximal branch of the aforementioned arteries, such as the ascending aorta. Opposing edges of the damping member 1302 can be secured to each other with a coupling device such as stitching/sutures 1310, stapling, or another coupling device such that the external diameter of the artery is reduced. In some embodiments, the coupling device can be made from an elastic material so that it can stretch to accommodate the pulse wave and absorb its energy. The elastically deformable damping member 1302 is adapted to radially expand during the systole stage and radially contract during the diastole stage. The damping member 1302 is secured such that an internal diameter of the elastically deformable material is smaller than an initial, outer diameter of the artery during a systole stage, but not smaller than an outer diameter of the artery during a diastole stage.

Figure 14:
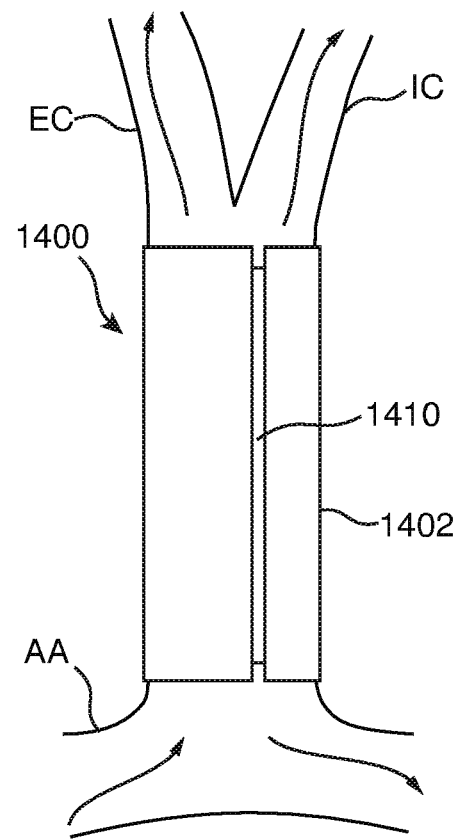

FIG. 14 depicts another embodiment of a damping device 1400 for treating an arterial blood vessel. The device 1400 can be structurally similar to the damping device 1300 shown in FIG. 13, with the exception that the two opposing edges of the elastically deformable damping member 1402 of FIG. 14 are secured to each other using a zip-lock type coupling mechanism 1410.

Figure 15:
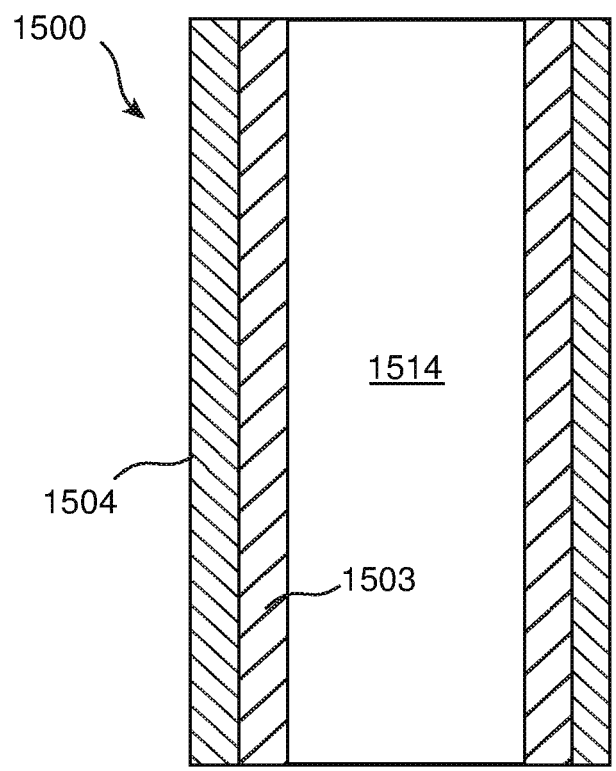
FIG. 15 is a cross-sectional view of another embodiment of a damping device in accordance with the present technology.

FIG. 15 shows another embodiment of a damping device 1500 configured in accordance with the present technology. The damping device 1500, includes a generally tubular anchoring member 1504 (e.g., a stent, a mesh, a braid, etc.) defining a lumen 1514 therethrough. The anchoring member may be made of a resilient, biocompatible material such as stainless steel, titanium, nitinol, etc. In some embodiments, the anchoring member 1504 is made of a shape memory and/or superelastic material. A radially outer surface of the anchoring member 1504 is configured to be positioned in apposition with an inner surface of an arterial wall. A radially inner surface of the anchoring member 1504 is lined or otherwise coated with an absorptive material 1503 (e.g., a cushioning material), such as an elastically deformable material, which is adapted to absorb shock. The lumen 1514 is configured to receive blood flow therethrough. The lumen 1514 is present when the anchoring member 1504 is radially expanded, but it may not be present in the initial, contracted configuration prior to deployment In some embodiments (not shown), the damping device can be a biocompatible gel which is injected around a portion of the left or right carotid artery or the brachiocephalic trunk. The gel increases the external pressure acting on the artery and thus reduces the external diameter of the artery. As blood pressure increases within the artery, the gel elastically deforms, such that the artery radially expands during the systole stage and radially contracts during the diastole stage.

Figure 16A:
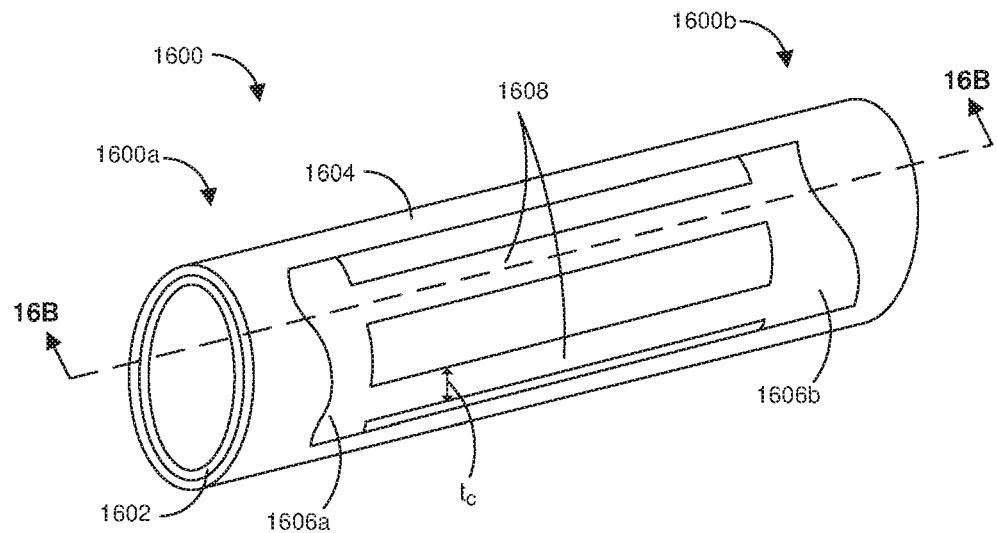
FIG. 16A is a perspective view of another embodiment of a damping device in accordance with the present technology.
Figure 16B:
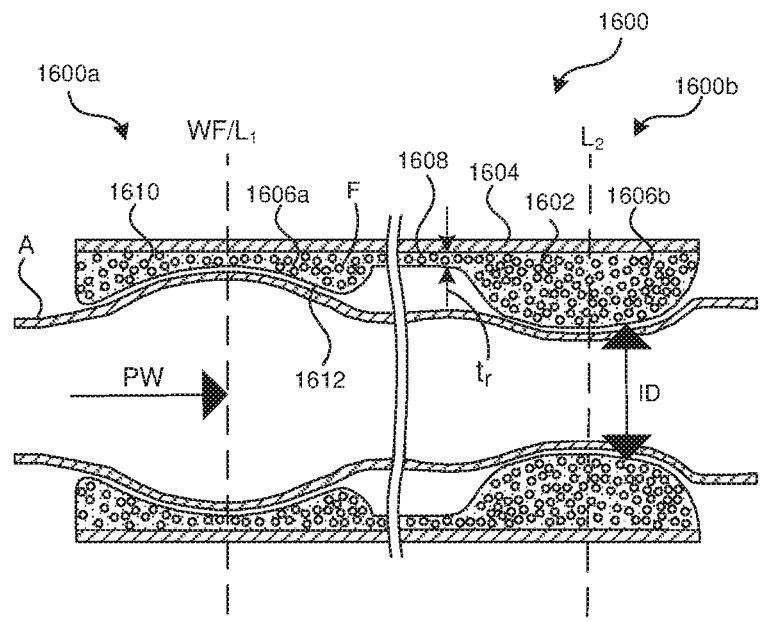
FIG. 16B is a cross-sectional view of the damping device shown in FIG. 16A, taken along line 16B-16B.

FIG. 16A is a perspective, cut-away view of a damping device 1600 in accordance with the present technology in a deployed, relaxed state. FIG. 16B is a cross-sectional view of the damping device 1600 positioned in an artery A during transmission of a pulse wave PW through the portion of the artery A surrounded by the damping device 1600. Referring to FIGS. 16A and 16B together, the damping device 1600 includes a damping member 1602 and a structural member 1604 coupled to the damping member 1602. In FIG. 16A, a middle portion of the structural member 1604 has been removed to show features of the structure of the damping member 1602. As shown in FIG. 16A, the damping device 1600 can have a generally cylindrical shape in the deployed, relaxed state. The damping device 1600 may be configured to wrap around the circumference of the artery with opposing longitudinal edges (not shown) secured to one another via sutures, staples, adhesive, and/or other suitable coupling devices. Alternatively, the damping device 1600 can have a longitudinal slit for receiving the artery therethrough. In either of the foregoing extravascular embodiments, the damping device 1600 is configured to be positioned around the circumference of the artery A so that the inner surface 1612 (FIG. 16B) is adjacent and/or in contact with the outer surface of the arterial wall. In other embodiments, the damping device 1600 can be configured to be positioned intravascularly (e.g., within the artery lumen) such that an outer surface of the damping device 1600 is adjacent and/or in contact with the inner surface of the arterial wall. In such intravascular embodiments, the inner surface 1612 of the damping member 1602 is adjacent or directly in contact with blood flowing through the artery A.

The structural member 1604 can be a generally cylindrical structure configured to expand from a low-profile state to a deployed state. The structural member 1604 is configured to provide structural support to secure the damping device 1600 to a selected region of the artery. In some embodiments, the structural member 1604 can be a stent formed from a laser cut metal, such as a superelastic and/or shape memory material (e.g., Nitinol) or stainless steel. All or a portion of the structural member 1604 can include a radiopaque coating to improve visualization of the device 1600 during delivery, and/or the structural member 1604 may include one or more radiopaque markers. In other embodiments, the structural member 1604 may comprise a mesh or woven (e.g., a braid) construction in addition to or in place of a laser cut stent. For example, the structural member 1604 can include a tube or braided mesh formed from a plurality of flexible wires or filaments arranged in a diamond pattern or other configuration. In some embodiments, all or a portion of the structural member 1604 can be covered by a graft material (such as Dacron) to promote sealing with the vessel wall. Additionally, all or a portion of the structural member 1604 can include one or more biomaterials.

In the embodiment shown in FIGS. 16A and 16B, the structural member 1604 is positioned radially outwardly of the damping member 1602 and extends along the entire length of the damping member 1602 (though a middle portion of the structural member 1604 is cut-away in FIG. 16A for illustrative purposes only). In other embodiments, the structural member 1604 and the damping member 1602 may have other suitable configurations. For example, the damping device 1600 can include more than one structural member 1604 (e.g., two structural members, three structural members, etc.). Additionally, in some embodiments the structural member(s) 1604 may extend along only a portion of the damping member 1602 such that a portion of the length of the damping member 1602 is not surrounded and/or axially aligned with any portion of the structural member 1604. Also, in some embodiments, all or a portion of the damping member 1602 may be positioned radially outwardly of all or a portion of the structural member 1604.

In the embodiment shown in FIGS. 16A and 16B, the damping member 1602 includes a proximal damping element 1606a and a distal damping element 1606b. The damping member 1602 may further include optional channels 1608 extending between the proximal and distal damping elements 1606a, 1606b. The channels 1608, for example, can extend in a longitudinal direction along the damping device 1600 and fluidly couple the proximal damping element 1606a to the distal damping element 1606b. The damping member 1602 may further include an abating substance 1610 configured to deform in response to fluid stress (such as blood flow), thereby absorbing at least a portion of the stress. For example, as best shown in FIG. 16B, in one embodiment the abating substance 1610 includes a plurality of fluid particles F (only one fluid particle labeled) contained in the proximal damping element 1606a, distal damping element 1606b, and channel(s) 1608. As used herein, the term "fluid" refers to liquids and/or gases, and "fluid particles" refers to liquid particles and/or gas particles. In some embodiments, the damping member 1602 is a gel, and the plurality of fluid particles F are dispersed within a network of solid particles. In other embodiments, the damping member 1602 may include only fluid particles F (e.g., only gas particles, only liquid particles, or only gas and liquid particles) contained within a flexible and/or elastic membrane that defines the proximal damping member 1606a, the distal damping member 1606b, and the channel(s) 1608. The viscosity and/or composition of the abating substance 1610 may be the same or may vary along the length and/or circumference of the damping member 1602.

In the embodiment shown in FIGS. 16A and 16B, the channels 1608 have a resting radial thickness $t_r$ and circumferential thickness $t_c$ (FIG. 16A) that is less than the resting radial thickness $t_r$ and circumferential thickness $t_c$, respectively, of the proximal and distal damping elements 1606a, 1606b. As best shown in FIG. 16A, in some embodiments the proximal and distal damping elements 1606a and 1606b may extend around the full circumference of the damping device 1600 and the channels 1608 may extend around only a portion of the circumference of the damping device 1600. In other embodiments, the channels 1608 can have a resting radial thickness $t_r$ that is generally the same as that of the proximal and distal damping elements 1606a, 1606b (see damping elements 1906a-c and channels 1908 in FIGS. 19A and 19B) and/or a resting circumferential thickness $t_c$ that is generally the same as that of the proximal and distal damping elements 1606a, 1606b.

Referring to FIG. 16B, when a pulse wave PW traveling through the artery A applies a stress at a first axial location $L_1$ along the length of the damping member 1602 (e.g., at wavefront WF), at least a portion of the fluid particles move away from the first axial location $L_1$ to a second axial location $L_2$ along the length of the damping member 1602. As such, at least a portion of the fluid particles are redistributed along the length of the damping member 1602 such that the inner diameter ID of the damping member 1602 increases at the first axial location $L_1$ while the inner diameter ID decreases at another axial location (e.g., $L_2$). For example, as the wavefront WF passes through the proximal portion 1600a of the device 1600, the portion of the artery A aligned with the wavefront WF dilates, thereby applying a stress to the proximal damping element 1606a and forcing at least some of the fluid particles in the proximal damping element 1606a to move distally within the damping member 1602. At least some of the displaced fluid particles are forced through the channel(s) 1608 and into the distal damping element 1606b, thereby increasing the volume of the distal damping element 1606b and decreasing the inner diameter ID of the damping device 1600 at the distal portion 1600b. The decreased inner diameter ID of the damping device 1600 provides an impedance to the blood flow that absorbs at least a portion of the energy in the pulse wave when the blood flow reaches the distal damping member 1606b. As the wavefront WF then passes through the distal portion 1600b of the device 1600, the portion of the artery A aligned with the wavefront WF dilates, thereby applying a stress to the distal damping element 1606b and forcing at least some of the fluid particles currently in the distal damping element 1606b to move proximally within the damping member 1602. At least some of the displaced fluid particles are forced through the channel(s) 1608 and into the proximal damping element 1606a, thereby increasing the volume of the proximal damping element 1606a and decreasing the inner diameter ID of the device 1600 at the proximal portion 1600a. Movement of the fluid particles and/or deformation of the damping member 1602 in response to the pulse wave absorbs at least a portion of the energy carried by the pulse wave, thereby reducing the stress on the arterial wall distal to the device.

When the damping member 1602 deforms in response to the pulse wave, the shape of the structural member 1604 may remain generally unchanged, thereby providing the support to facilitate redistribution of the fluid particles within and along the damping member 1602. In other embodiments, the structural member 1604 may also deform in response to the local fluid stress.

Figure 17A:
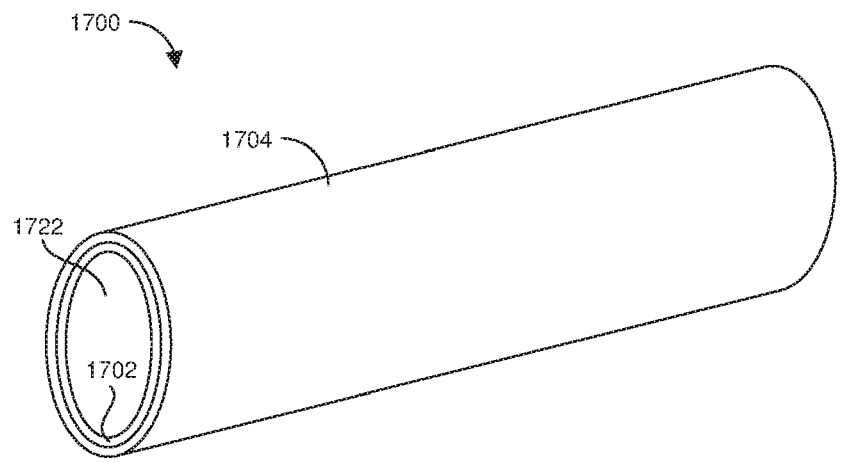
FIG. 17A is a perspective view of another embodiment of a damping device in accordance with the present technology.
Figure 17B:
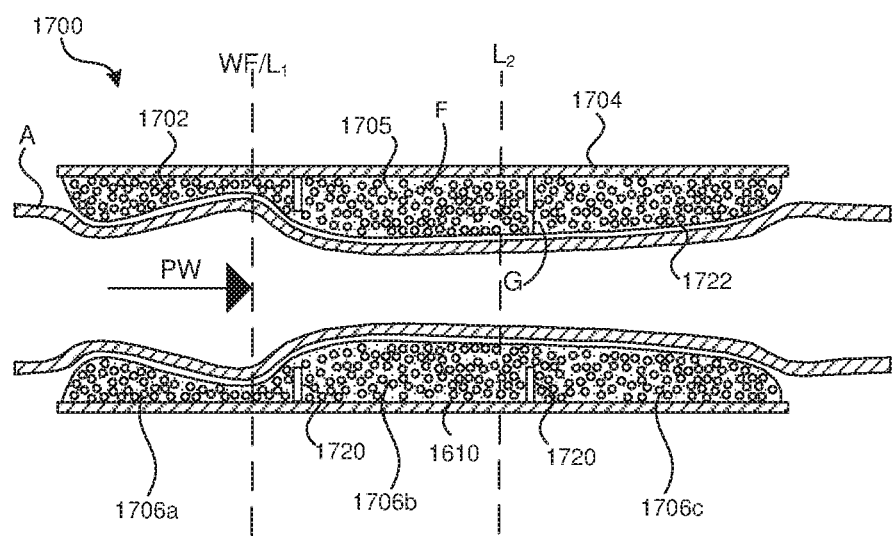
FIG. 17B is a cross-sectional view of the damping device shown in FIG. 17A.

FIG. 17A is a perspective view of another embodiment of a damping device 1700 in accordance with the present technology. FIG. 17B is a cross-sectional view of the damping device 1700 positioned in an artery A during transmission of a pulse wave PW through the portion of the artery A surrounded by the damping device 1700. The damping device 1700 can include a structural member 1704 and a damping member 1702. The structural member 1704 can be generally similar to the structural member 1604 shown in FIGS. 16A and 16B. The damping member 1702 is defined by a single chamber 1705 including an abating substance 1610 and a plurality of baffles 1720 that separate the chamber 1705 into three fluidically-coupled compartments 1706a, 1706b, and 1706c. The baffles 1720 extend only a portion of the radial thickness of the damping member 1702, thereby leaving a gap G between the end of the baffles 1720 and an inner wall 1722 of the damping member 1702. In other embodiments, the damping device 1700 can include more or fewer compartments (e.g., a single, tubular compartment (no baffles), two compartments, four compartments, etc.). Moreover, the baffles 1720 may extend around all or a portion of the circumference of the damping member 1702.

Figure 18A:
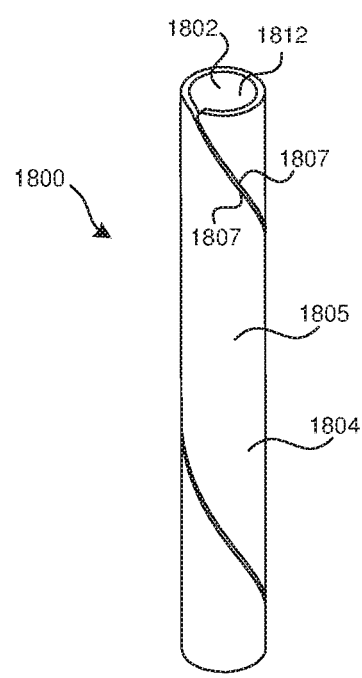
FIG. 18A is a perspective view of another embodiment of a damping device in accordance with the present technology.
Figure 18B:
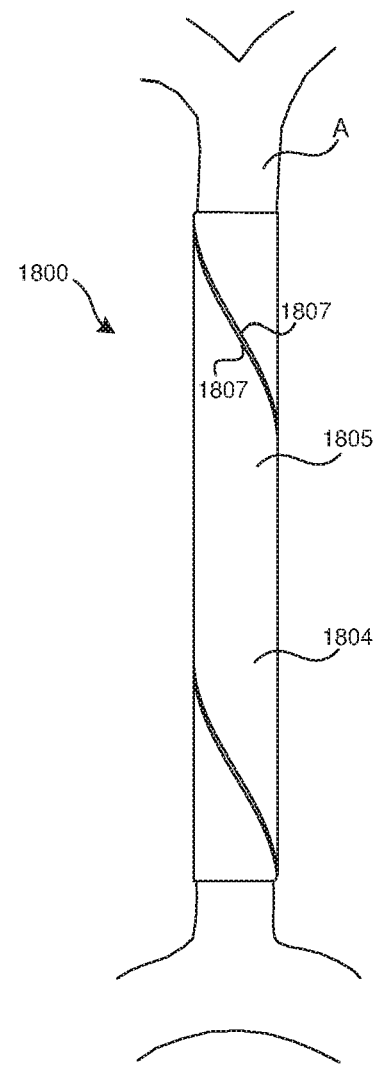
FIG. 18B is a front view of the damping device shown in FIG. 18A, shown in a deployed state positioned around a blood vessel.

FIG. 18A is a perspective view of another embodiment of a damping device 1800 in accordance with the present technology, and FIG. 18B is a front view of the damping device 1800, shown in a deployed state positioned around an artery A. Referring to FIGS. 18A-18B together, the damping device 1800, in a deployed, relaxed state, includes a generally tubular sidewall 1805 that defines a lumen. The damping device 1800 can be formed of a generally parallelogram-shaped element that is wrapped around a mandrel in a helical configuration and heat set. In other embodiments, the damping device 1800 can have other suitable shapes and configurations in the unfurled, non-deployed state. As shown in FIG. 18B, in the deployed state, the damping device 1800 is configured to be wrapped helically along or around the circumference of an artery supplying blood to the brain. Opposing longitudinal edges 1807 of the damping device 1800 come together in the deployed state to form a helical path along the longitudinal axis of the artery A. The damping device 1800 can include any of the coupling devices described with respect to FIGS. 13-15 to secure all or a portion of the opposing longitudinal edges to one another.

As best shown in FIG. 18A, the sidewall 1805 of the damping device 1800 includes a structural member 1804 and a damping member 1802. The structural member 1804 can be generally similar to the structural member 1604 shown in FIGS. 16A and 16B, except the structural member 1804 of FIGS. 18A and 18B has a helical configuration in the deployed state. The damping member 1802 can be generally similar to any of the damping members described herein, especially those described with respect to FIGS. 13-17B and 19A and 19B. In the embodiment shown in FIGS. 18A and 18B, the damping member 1802 is positioned radially inwardly of the structural member 1804 when the damping device 1800 is in the deployed state. In other embodiments, the damping member 1802 may be positioned radially outwardly of the structural member 1804 when the damping device 1800 is in the deployed state.

The damping device 1800 may be configured to wrap around the circumference of the artery A so that the inner surface 1812 (FIG. 18A) is adjacent and/or in contact with the outer surface of the arterial wall. In other embodiments, the damping device 1800 can be configured to be positioned intravascularly (e.g., within the artery lumen) such that an outer surface of the damping device 1800 is adjacent and/or in contact with the inner surface of the arterial wall. In such intravascular embodiments, the inner surface 1812 of the damping member 1802 is adjacent or directly in contact with blood flowing through the artery A.

Figure 19A:
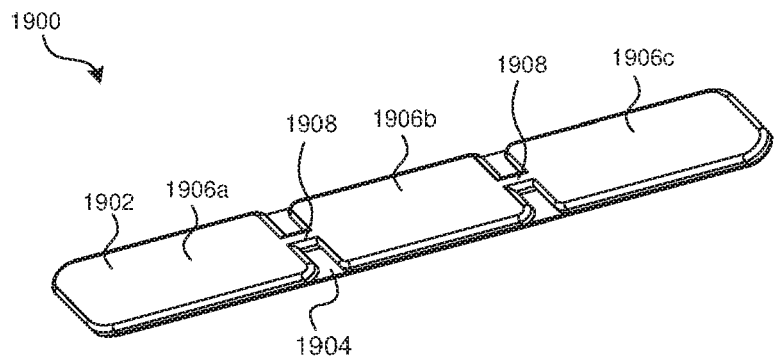
FIG. 19A is a perspective view of a damping device in accordance with another embodiment of the present technology, shown in an unwrapped state.
Figure 19B:
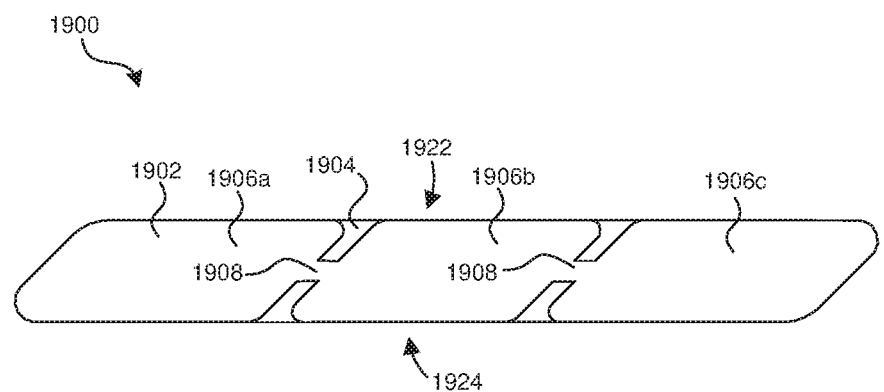
FIG. 19B is a top view of the damping device shown in FIG. 19A, shown in an unwrapped state.

FIGS. 19A and 19B are perspective and top views, respectively, of a damping device 1900 that can define one embodiment of the damping device 1800 shown in FIGS. 18A and 18B. In FIGS. 19A and 19B, the damping device 1900 is shown in an unfurled, non-deployed state. The damping device 1900 includes a damping member 1902 having a plurality of chambers 1906a, 1906b, 1906c spaced apart along a longitudinal dimension of the damping device 1900 in the unfurled state. The chambers 1906a, 1906b, 1906c may be fluidly coupled by channels 1908 extending between adjacent chambers. The damping device 1900 can thus operate in a manner similar to the damping device 1600 where an abating substance (not shown in FIGS. 19A and 19B) in the chambers 1906a-c moves through the channels 1908 to inflated/deflate individual chambers in response to a pressure wave traveling through the blood vessel. The displacement of the abating substance within the chambers 1906a-c attenuates the energy of the pulse wave to reduce the impact of the pulse wave distally of the damping device 1900.

IV. EXAMPLES

The following examples are illustrative of several embodiments of the present technology:

1. A device for treating or slowing the progression of dementia, comprising:
    a flexible, compliant damping member configured to be intravascularly positioned within an artery at a treatment site, the damping member being transformable between a low-profile state for delivery to the treatment site and an expanded state, wherein the damping member includes a generally tubular sidewall having (a) an outer surface, (b) an inner surface defining a lumen configured to direct blood flow, (c) a first end portion, (d) a second end portion opposite the first end portion along the length of the damping member, and (e) a damping region between the first and second end portions, wherein the inner surface and outer surface are spaced apart by a distance that is greater at the damping region than at either of the first or second end portions; and a first anchoring member coupled to the first end portion of the damping member and a second anchoring member coupled to the second end portion of the damping member, wherein the first and second anchoring members, in a deployed state, extend radially to a deployed diameter configured to contact a portion of the arterial wall at the treatment site, thereby securing the damping member at the treatment site, and wherein the first and second anchoring members extend along only a portion of the length of the damping member such that at least a portion of the damping region is exposed between the first and second anchoring members and allowed to expand to a diameter greater than the deployed diameter.

2. The device of example 1 wherein the damping member is configured to deform in response to a change in blood pressure.

3. The device of example 1 or example 2 wherein, at a location along the damping member coincident with a leading end of a pulse pressure wave, the distance between the inner surface and the outer surface of the damping member decreases in response to the pressure.

4. The device of any one of examples 1-3 wherein the lumen of the damping member has an hourglass shape.

5. The device of any one of examples 1~4 wherein the outer surface is generally cylindrical and the inner surface is undulating.

6. The device of any one of examples 1-5 wherein each of the first and second anchoring members is an expandable stent.

7. The device of any one of examples 1-5 wherein the each of the first and second anchoring members is an expandable mesh.

8. The device of any one of examples 1-5 wherein each of the first and second anchoring members is at least one of an expandable stent and an expandable mesh.

9. The device of any one of examples 1-8 wherein each of the first and second anchoring members is positioned around a circumference of the damping member.

10. The device of any one of examples 1-8 wherein at least a portion of each of the first and second anchoring members is positioned within the damping member and extends through at least a portion of the thickness of the sidewall.

11. The device of any one of examples 1-10 wherein the damping region is a first damping region, and wherein the damping member includes a plurality of damping regions between the first and second end portions.

12. The device of any one of examples 1-11 wherein at least one of the first and second anchoring members comprise a plurality of fixation devices extending radially outwardly from the outer surface of the damping device.

13. The device of any one of examples 1-12 wherein the device is configured to be positioned at a treatment site within the left common carotid artery.

14. The device of any one of examples 1-13 wherein the device is configured to be positioned at a treatment site within the right common carotid artery.

15. The device of any one of examples 1-14 wherein the device is configured to treat Alzheimer's disease.

16. The device of any one of examples 1-15 wherein the device is configured to reduce the occurrence of microbleeds in one or more branches of the artery downstream from the treatment site.

17. A device for treating dementia, comprising:
a damping member configured to be intravascularly positioned within an artery at a treatment site and having a lumen configured to direct blood flow to distal vasculature, the damping member being transformable between a low-profile state for delivery to the treatment site and an expanded state, wherein the damping member includes a damping region having a pressure limiter projecting laterally inwardly into the lumen to distribute pressure downstream from the damping member when a pulse pressure wave propagates along the damping member during systole; and an anchoring member coupled to the damping member, wherein the anchoring member, in a deployed state, is configured to extend outwardly to a deployed diameter and contact a portion of the blood vessel wall at the treatment site, thereby securing the damping member at the treatment site, wherein the anchoring member extends along only a portion of the length of the damping member such that the damping region of the damping member is allowed to extend radially outward beyond the deployed diameter of the anchoring member.

18. The device of example 17 wherein the damping member is configured to deform in response to a change in blood pressure.

19. The device of example 17 or example 18 wherein, at a location along the damping member coincident with a leading end of a pulse pressure wave, the distance between the inner surface and the outer surface of the damping member decreases in response to the pressure.

20. The device of any one of examples 17-19 wherein the lumen of the damping member has an hourglass shape.

21. The device of any one of examples 17-20 wherein the anchoring member is an expandable stent.

22. The device of any one of examples 17-20 wherein the anchoring member is an expandable mesh.

23. The device of any one of examples 17-20 wherein the anchoring member is at least one of an expandable stent and an expandable mesh.

24. The device of any one of examples 17-23 wherein the anchoring member is positioned around a circumference of the damping member.

25. The device of any one of examples 17-23 wherein at least a portion of the anchoring member is positioned within the damping member and extends through at least a portion of the thickness of the sidewall.

26. The device of any one of examples 17-25 wherein the damping region is a first damping region, and wherein the damping member includes a plurality of damping regions between the first and second end portions.

27. The device of any one of examples 17-26 wherein the anchoring member includes a plurality of fixation devices extending radially outwardly from the outer surface of the damping device.

28. The device of any one of examples 17-27 wherein the device is configured to be positioned at a treatment site within the left common carotid artery.

29. The device of any one of examples 17-28 wherein the device is configured to be positioned at a treatment site within the right common carotid artery.

30. The device of any one of examples 17-29 wherein the device is configured to treat Alzheimer's disease.

31. The device of any one of examples 17-29 wherein the device is configured to reduce the occurrence of microbleeds in portions of the blood vessel downstream from the treatment site.

32. A device for treating dementia, comprising:
a flexible, compliant damping member configured to be intravascularly positioned within an artery at a treatment site, the damping member being transformable between a low-profile state for delivery to the treatment site and an expanded state, wherein the damping member includes a generally tubular sidewall having (a) an outer surface, (b) an inner surface defining a lumen configured to direct blood flow, (c) a first end portion, (d) a second end portion opposite the first end portion along the length of the damping member, and (e) a damping region between the first and second end portions, wherein the inner surface and outer surface are spaced apart by a distance that is greater at the damping region than at either of the first or second end portions; and
a first anchoring member coupled to the first end portion of the damping member and a second anchoring member coupled to the second end portion of the damping member, wherein the first and second anchoring members, in a deployed state, extend radially to a deployed diameter configured to contact a portion of the blood vessel wall at the treatment site, thereby securing the damping member at the treatment site, and wherein, when blood flows through the damping member during systole, the damping member absorbs a portion of the pulsatile energy of the blood, thereby reducing a magnitude of a pulse pressure transmitted to a portion of the blood vessel distal to the damping device.

33. A device for treating a blood vessel, comprising:
an anchoring system having a first portion and a second portion; and
a cushioning member located between the first and second portions of the anchoring system such that a portion of the cushioning member is not constrained by the anchoring system, and wherein the cushioning member is configured to absorb pulsatile energy transmitted by blood flowing with the vessel.

34. The device of example 33 wherein the cushioning member is configured to expand in response to an increase of blood pressure within the vessel, and relax as the blood pressure within the vessel subsequently decreases.

35. A device for treating a blood vessel, comprising:
an endovascular cushioning device having a proximal anchor and a distal anchor, each of the proximal and distal anchors being configured to abut against an inner wall of a major artery; and
an elastically deformable member extending between the proximal and distal anchors,
wherein the elastically deformable member is configured to expand in response to an increase of blood pressure within the vessel, and relax as the blood pressure within the vessel subsequently decreases.

36. The device of example 35 wherein a portion of the elastically deformable membrane located longitudinally between the proximal and distal anchors defines a region of reduced internal cross-sectional area relative to the proximal and distal anchors when the elastically deformable membrane is radially relaxed.

37. The device of example 35 or example 36 wherein the proximal and distal anchors are each radially expandable between a first diameter before deployment and a second diameter after deployment.

38. The device of any one of examples 35-37, further comprising one or more threads secured to the proximal anchor.

39. The device of example 38 wherein each thread is secured to an eyelet.

40. A device for treating an artery selected from a left common carotid artery, a right common carotid artery, a brachiocephalic artery, the ascending aorta, an internal carotid artery, or an abdominal aorta, the device comprising:
a wrap fabricated from an elastically deformable material, and
an engagement formation adapted to secure two opposing edges of the wrap around the artery,
wherein the elastically deformable material is configured to radially expand during a systole stage and radially contract during a diastole stage.

41. The device of example 40 wherein the engagement formation includes sutures and/or staples.

42. The device of example 41 wherein the engagement formation includes a zip lock.

43. A device for treating a left common carotid artery, a right common carotid artery, a brachiocephalic artery, or an ascending aorta, the device comprising:
a proximal anchor configured to be wrapped around the artery;
a distal anchor configured to be wrapped around the artery and longitudinally spaced relative to the proximal anchor; and
a helical band adapted to be wound around the artery, the helical band having a first end securable to the proximal anchor and an opposing second end securable to the distal anchor, wherein the helical band is adapted to radially expand during a systole stage and radially contract during a diastole stage.

44. A device for treating or slowing the effects of dementia, comprising:
a damping member having a low-profile state and a deployed state, wherein, in the deployed state, the damping member comprises a deformable, generally tubular sidewall having an outer surface and an inner surface that is undulating in a longitudinal direction, and wherein the sidewall is configured to be positioned in apposition with a blood vessel wall to absorb pulsatile energy transmitted by blood flowing through the blood vessel.

45. The device of example 1 wherein the damping member is configured to be positioned in apposition with at least one of a left common carotid artery, a right common carotid artery, and a brachiocephalic artery.

46. The device of example 44 or example 45 wherein the damping member is configured to be positioned in apposition with an ascending aorta.

47. The device of any one of examples 44-46 wherein the damping member is configured to be positioned in apposition with an inner surface of the blood vessel wall.

48. The device of any one of examples 44-46 wherein the damping member is configured to be positioned in apposition with an outer surface of the blood vessel wall.

49. The device of any one of examples 44-48 wherein the sidewall has an inner diameter, and, when the damping member is in a deployed state, the inner diameter increases then decreases in an axial direction.

50. The device of any one of examples 44-49 wherein the cross-sectional area decreases then increases in longitudinal direction.

51. The device of any one of examples 44-50 wherein the outer surface has a generally cylindrical shape.

52. The device of any one of examples 44-50 wherein the outer surface has an undulating shape.

53. The device of any one of examples 44-52, further comprising an anchoring member coupled to the damping member and axially aligned with only a portion of the damping member, wherein the anchoring member is configured to engage the blood vessel wall and secure the damping member to the blood vessel wall.

54. The device of any one of examples 44-53 wherein the anchoring member is a first anchoring member and the device further comprises a second anchoring member coupled to the damping member, and wherein the second anchoring member:
 is axially aligned with only a portion of the damping member, and
 is spaced apart from the first anchoring member along the longitudinal axis of the damping member.

55. The device of any one of examples 44-54 wherein, when the damping member is positioned adjacent the blood vessel wall, the damping member does not constrain the diameter of the blood vessel wall.

56. A device for treating or slowing the effects of dementia, comprising:
 an elastic member having a low-profile state for delivery to a treatment site at a blood vessel wall and a deployed state, wherein, in the deployed state, the elastic member is configured to abut an arterial wall and form a generally tubular structure having an inner diameter, an outer diameter, an outer surface, and an undulating inner surface, and wherein at least one of the outer diameter and the inner diameter increases and decreases in response to an increase and a decrease in pulse pressure within the blood vessel, respectively.

57. The device of example 56 wherein the elastic member is configured to be positioned in apposition with at least one of a left common carotid artery, a right common carotid artery, and a brachiocephalic artery.

58. The device of example 56 or example 57 wherein the elastic member is configured to be positioned in apposition with an ascending aorta.

59. The device of any one of examples 56-58 wherein the elastic member is configured to be positioned in apposition with an inner surface of the blood vessel wall.

60. The device of any one of examples 56-58 wherein the elastic member is configured to be positioned in apposition with an outer surface of the blood vessel wall.

61. The device of any one of examples 56-60 wherein the sidewall has an inner diameter, and, when the elastic member is in a deployed state, the inner diameter increases then decreases in an axial direction.

62. The device of any one of examples 56-61 wherein the cross-sectional area decreases then increases in longitudinal direction.

63. The device of any one of examples 56-62 wherein the outer surface has a generally cylindrical shape.

64. The device of any one of examples 56-62 wherein the outer surface has an undulating shape.

65. The device of any one of examples 56-64, further comprising an anchoring member coupled to the elastic member and axially aligned with only a portion of the elastic member, wherein the anchoring member is configured to engage the blood vessel wall and secure the elastic member to the blood vessel wall.

66. The device of example 65 wherein the anchoring member is a first anchoring member and the device further comprises a second anchoring member coupled to the elastic member, and wherein the second anchoring member:
 is axially aligned with only a portion of the elastic member, and
 is spaced apart from the first anchoring member along the longitudinal axis of the elastic member.

67. The device of any one of examples 56-66 wherein, when the elastic member is positioned adjacent the blood vessel wall, the elastic member does not constrain the diameter of the blood vessel wall.

68. A device for treating or slowing the effects of dementia, comprising:
 a damping member including an abating substance, the damping member having a low-profile configuration and a deployed configuration, wherein, when the damping member is in the deployed configuration, the damping member forms a generally tubular structure configured to be positioned along the circumference of an artery such that, when a pulse wave traveling through the artery applies a stress at a first axial location along the length of the tubular structure, at least a portion of the abating substance moves away from the first location to a second axial location along the length of the tubular structure.

69. The device of example 68, further comprising a structural element coupled to the damping member.

70. The device of example 68 or example 69 wherein, in the deployed state, the damping member is configured to wrap around at least a portion of the circumference of the artery.

71. The device of any one of examples 68-70 wherein, in the deployed state, the device has a pre-set helical configuration.

72. The device of any one of examples 68-71 wherein the damping member includes a liquid.

73. The device of any one of examples 68-72 wherein the damping member includes a gas.

74. The device of any one of examples 68-73 wherein the damping member includes a gel.

75. The device of any one of examples 68-74 wherein the damping member, in the deployed configuration, is configured to be positioned in apposition with an outer surface of the arterial wall.

76. The device of any one of examples 68-74 wherein the damping member, in the deployed configuration, is configured to be positioned around the arterial wall such that an inner surface of the damping member is in contact with blood flowing through the artery.

77. A device for treating or slowing the effects of dementia, comprising:
 a damping member including a plurality of fluid particles, the damping member having a low-profile configuration and a deployed configuration, wherein, when the damping member is in the deployed configuration, the damping member is configured to be positioned along the circumference of an artery at a treatment site along a length of the artery,
 wherein, when the damping member is in a deployed configuration and positioned at the treatment site, a wavefront traveling through the length of the artery redistributes at least a portion of the fluid particles along the length of the damping member such that the inner diameter of the damping member increases at the axial location along the damping member aligned with the wavefront while the inner diameter of the damping member at another axial location along the damping member decreases.

78. The device of example 77, further comprising a structural element coupled to the damping member.

79. The device of example 77 or example 78 wherein, in the deployed state, the damping member is configured to wrap around at least a portion of the circumference of the artery.

80. The device of any one of examples 77-79 wherein, in the deployed state, the device has a pre-set helical configuration.

81. The device of any one of examples 77-80 wherein the damping member includes a liquid.

82. The device of any one of examples 77-81 wherein the damping member includes a gas.

83. The device of any one of examples 77-82 wherein the damping member includes a gel.

84. The device of any one of examples 77-83 wherein the damping member, in the deployed configuration, is configured to be positioned in apposition with an outer surface of the arterial wall.

85. The device of any one of examples 77-84 wherein the damping member, in the deployed configuration, is configured to be positioned around the arterial wall such that an inner surface of the damping member is in contact with blood flowing through the artery.

86. A method for treating or slowing the effects of dementia, comprising:
positioning a damping device in apposition with at least one of the brachiocephalic artery, the right common carotid artery, the left common carotid artery, the ascending aorta, and the aortic arch, the damping device comprising an elastic, generally tubular sidewall whereby the damping device absorbs pulsatile energy transmitted by blood flowing through the at least one of the brachiocephalic artery, the right common carotid artery, the left common carotid artery, the ascending aorta, and the aortic arch.

87. A method for treating or slowing the effects of dementia, comprising:
positioning a damping device in apposition with the wall of an artery that delivers blood to the brain, the damping device comprising an elastic, generally tubular sidewall having an outer surface and an undulating inner surface; and
in response to a pulse pressure wave in blood flowing through the blood vessel, a contour of at least one of the inner surface and the outer surface changes.

88. A method for treating at least one of the brachiocephalic artery, the right common carotid artery, the left common carotid artery, the ascending aorta, and the aortic arch, the method comprising:
positioning a damping device in apposition with a blood vessel wall, the damping device comprising an elastic, generally tubular sidewall;
expanding at least one of the inner diameter and the outer diameter of the damping device in response to an increase in pulse pressure; and
contracting at least one of the inner diameter and the outer diameter of the damping device in response to a decrease in pulse pressure.

89. A method of treating a blood vessel, comprising:
inserting a catheter into a vessel and directing a tip of the catheter to a desired vascular location;
transferring a distal anchor from within the catheter tip into the vessel;
expanding the distal anchor such that a radially outer portion of the distal anchor engages with an inner wall of the vessel;
withdrawing the catheter slightly and transferring a proximal anchor from the tip of the catheter into the vessel;
longitudinally positioning the proximal anchor at a desired location;
expanding the proximal anchor such that a radially outer portion of the proximal anchor engages with an inner wall of the vessel, wherein an elastically deformable member extends longitudinally between the proximal and distal anchors.

90. The method of example 89 wherein transferring the distal anchor includes advancing the distal anchor from the tip of the catheter.

91. The method of example 89 or example 90 wherein transferring the distal anchor includes withdrawing the tip of the catheter whilst the distal anchor remains at a generally constant longitudinal position within the vessel, and exits from the tip of the catheter.

92. The method of any one of examples 89-91 wherein longitudinally positioning the proximal anchor includes applying a first tensile force to one or more threads frangibly secured to the proximal anchor.

93. The method of example 92, further including frangibly rupturing the thread(s) after expanding the proximal anchor by applying a second tensile force which is greater than the first tensile force.

94. The method of example 92, further including disengaging a ring, latch or clasp secured to the thread(s) after expanding the proximal anchor in order to disengage the thread from the proximal anchor.

95. The method of any one of examples 89-94, further including imaging to determine the location of the proximal and/or distal anchors.

96. A method of treating a blood vessel selected from a left common carotid artery, a right common carotid artery or a brachiocephalic artery, a carotid artery, a branch of any of the foregoing and an ascending aorta, the method comprising:
wrapping an elastically deformable material around the artery; and
attaching a first edge of the elastically deformable material to an opposing second edge of the elastically deformable material such that an internal diameter of the elastically deformable material is smaller than an initial outer diameter of the artery during a systole stage.

97. A method for treating dementia, comprising:
intravascularly positioning a damping device within an artery at a treatment site, wherein the damping device includes an anchoring member coupled to an elastic, tubular damping member defining a lumen therethrough;
expanding the anchoring member and the damping member from a low profile state to an expanded state such that at least the anchoring member is in apposition with the arterial wall at the treatment site; and
changing a contour of the damping member in response to a pulse pressure wave in blood flow through the damping member.

98. The method of example 97, further comprising reducing a magnitude of the pulse pressure transmitted to a portion of the blood vessel distal to the damping device.

99. The method of example 98 wherein reducing a magnitude of the pulse pressure includes absorbing a portion of the pulsatile energy of blood flowing through the artery.

100. The method of any one of examples 97-99 wherein changing a contour of the damping member includes increasing an inner diameter of the lumen damping member while an outer diameter of the damping member remains generally constant.

101. The method of any one of examples 97-99 wherein changing a contour of the damping member includes increasing an inner diameter and an outer diameter of the lumen of the damping member.

102. The method of any one of examples 97-99 wherein changing a contour of the damping member includes decreasing a distance between an inner surface of the damping member and an outer surface of the damping member.

103. The method of example 1 wherein intravascularly positioning a damping device includes intravascularly positioning a damping device within a left common carotid artery at a treatment site.

104. The method of any one of examples 97-103 wherein intravascularly positioning a damping device includes intravascularly positioning a damping device within a right common carotid artery at a treatment site.

105. The method of any one of examples 97-104 wherein expanding the anchoring member and expanding the damping member occurs simultaneously.

106. The method of any one of examples 97-105 wherein expanding the anchoring member includes expanding the anchoring member with a balloon.

107. The method of any one of examples 97-105 wherein expanding the anchoring member includes withdrawing a sheath to expose the anchoring member to allow the anchoring member to self-expand.

108. The method of any one of examples 97-107 wherein expanding the damping member includes expanding the damping member with a balloon.

109. The method of any one of examples 97-107 wherein expanding the damping member includes withdrawing a sheath to expose the damping member to allow the anchoring member to self-expand.

110. The method of any one of examples 97-109 wherein expanding the anchoring member forces the damping member to expand.

111. The method of any one of examples 97-110 wherein:
the damping device is a first damping device,
the first damping device is intravascularly positioned at a first arterial location, and
the method further comprises intravascularly positioning a second damping device at a second arterial location different than the first arterial location.

112. The method of example 111 wherein the first arterial location is one of a left common carotid artery, a right common carotid artery, an external carotid artery, an internal carotid artery, and an ascending aorta, and the second arterial location is one of a left common carotid artery, a right common carotid artery, an external carotid artery, an internal carotid artery, and an ascending aorta.

113. The method of example 111 wherein the first arterial location is a left common carotid artery and the second arterial location is a right common carotid artery.

114. A method for treating or slowing the effects of dementia, comprising:
positioning a damping member along a length of an artery, the damping member including an abating substance; and
in response to a pulse wave traveling through blood in the artery, redistributing at least a portion of the abating compound along the length of the damping member, thereby attenuating at least a portion of the energy of the pulse wave in the blood.

115. A method for treating or slowing the effects of dementia, comprising:
positioning a damping member along a length of an artery, the damping member including a plurality of fluid particles; and
moving a portion of the fluid particles away from an axial location along the damping member aligned a wavefront of a pulse wave, thereby increasing the inner diameter of the damping member.

116. A device for treating or slowing the progression of dementia, comprising:
a flexible, compliant damping member configured to be intravascularly positioned within an artery at a treatment site, the damping member being transformable between a low-profile state for delivery to the treatment site and an expanded state, wherein the damping member includes a generally tubular sidewall having (a) an outer surface, (b) an inner surface defining a lumen configured to direct blood flow, (c) a first end portion, (d) a second end portion opposite the first end portion along the length of the damping member, and (e) a damping region between the first and second end portions, wherein the inner surface and outer surface are spaced apart by a distance that is greater at the damping region than at either of the first or second end portions; and
a first anchoring member coupled to the first end portion of the damping member and a second anchoring member coupled to the second end portion of the damping member, wherein the first and second anchoring members, in a deployed state, extend radially to a deployed diameter configured to contact a portion of the arterial wall at the treatment site, thereby securing the damping member at the treatment site, and wherein the first and second anchoring members extend along only a portion of the length of the damping member such that at least a portion of the damping region is exposed between the first and second anchoring members and allowed to expand to a diameter greater than the deployed diameter.

117. The device of example 116 wherein the damping member is elastically deformable, and is configured to deform in response to a change in blood pressure.

118. The device of example 116 or example 117 wherein, at a location along the damping member coincident with a leading end of a pulse pressure wave, the distance between the inner surface and the outer surface of the damping member decreases in response to the pressure.

119. The device of any one of examples 116-118 wherein the lumen of the damping member has an hourglass shape.

120. The device of any one of example 116-119 wherein the outer surface is generally cylindrical and the inner surface is undulating.

121. The device of any one of examples 116-120 wherein each of the first and second anchoring members is an expandable stent.

122. The device of any one of examples 116-120 wherein the each of the first and second anchoring members is an expandable mesh.

123. The device of any one of examples 116-120 wherein each of the first and second anchoring members is at least one of an expandable stent and an expandable mesh.

124. The device of any one of examples 116-123 wherein each of the first and second anchoring members is positioned around a circumference of the damping member.

125. The device of any one of examples 116-124 wherein at least a portion of each of the first and second anchoring members is positioned within the damping member and extends through at least a portion of the thickness of the sidewall.

126. The device of any one of examples 116-125 wherein the damping region is a first damping region, and wherein the damping member includes a plurality of damping regions between the first and second end portions.

127. The device of any one of examples 116-126 wherein at least one of the first and second anchoring members comprise a plurality of fixation devices extending radially outwardly from the outer surface of the damping device.

128. The device of any one of examples 116-127 wherein the device is configured to be positioned at a treatment site within the left common carotid artery.

129. The device of any one of examples 116-127 wherein the device is configured to be positioned at a treatment site within the right common carotid artery.

130. The device of any one of examples 116-129 wherein the device is configured to treat Alzheimer's disease.

131. The device of any one of examples 116-129 wherein the device is configured to reduce the occurrence of microbleeds in one or more branches of the artery downstream from the treatment site.

132. A device for treating dementia, comprising:
a damping member configured to be intravascularly positioned within an artery at a treatment site and having a lumen configured to direct blood flow to distal vasculature, the damping member being transformable between a low-profile state for delivery to the treatment site and an expanded state, wherein the damping member includes a damping region having a pressure limiter projecting laterally inwardly into the lumen to distribute pressure downstream from the damping member when a pulse pressure wave propagates along the damping member during systole; and
an anchoring member coupled to the damping member, wherein the anchoring member, in a deployed state, is configured to extend outwardly to a deployed diameter and contact a portion of the blood vessel wall at the treatment site, thereby securing the damping member at the treatment site, wherein the anchoring member extends along only a portion of the length of the damping member such that the damping region of the damping member is allowed to extend radially outward beyond the deployed diameter of the anchoring member.

133. The device of example 132 wherein the damping member is elastically deformable, and is configured to deform in response to a change in blood pressure.

134. The device of example 132 or 133 wherein, at a location along the damping member coincident with a leading end of a pulse pressure wave, the distance between the inner surface and the outer surface of the damping member decreases in response to the pressure.

135. The device of any one of examples 132-134 wherein the lumen of the damping member has an hourglass shape.

136. The device of any one of examples 132-135 wherein the anchoring member is an expandable stent.

137. The device of any one of examples 132-136 wherein the anchoring member is an expandable mesh.

138. The device of any one of examples 132-137 wherein the anchoring member is at least one of an expandable stent and an expandable mesh.

139. The device of any one of examples 132-138 wherein the anchoring member is positioned around a circumference of the damping member.

140. The device of any one of examples 132-139 wherein at least a portion of the anchoring member is positioned within the damping member and extends through at least a portion of the thickness of the sidewall.

141. The device of any one of examples 132-140 wherein the damping region is a first damping region, and wherein the damping member includes a plurality of damping regions between the first and second end portions.

142. The device of any one of examples 132-141 wherein the anchoring member includes a plurality of fixation devices extending radially outwardly from the outer surface of the damping device.

143. The device of any one of examples 132-142 wherein the device is configured to be positioned at a treatment site within the left common carotid artery.

144. The device of any one of examples 132-142 wherein the device is configured to be positioned at a treatment site within the right common carotid artery.

145. The device of any one of examples 132-144 wherein the device is configured to treat Alzheimer's disease.

146. The device of any one of examples 132-145 wherein the device is configured to reduce the occurrence of microbleeds in portions of the blood vessel downstream from the treatment site.

147. A device for treating dementia, comprising:
a flexible, compliant damping member configured to be intravascularly positioned within an artery at a treatment site, the damping member being transformable between a low-profile state for delivery to the treatment site and an expanded state, wherein the damping member includes a generally tubular sidewall having (a) an outer surface, (b) an inner surface defining a lumen configured to direct blood flow, (c) a first end portion, (d) a second end portion opposite the first end portion along the length of the damping member, and (e) a damping region between the first and second end portions, wherein the inner surface and outer surface are spaced apart by a distance that is greater at the damping region than at either of the first or second end portions; and
a first anchoring member coupled to the first end portion of the damping member and a second anchoring member coupled to the second end portion of the damping member, wherein the first and second anchoring members, in a deployed state, extend radially to a deployed diameter configured to contact a portion of the blood vessel wall at the treatment site, thereby securing the damping member at the treatment site, and
wherein, when blood flows through the damping member during systole, the damping member absorbs a portion of the pulsatile energy of the blood, thereby reducing a magnitude of a pulse pressure transmitted to a portion of the blood vessel distal to the damping device.

148. A device for treating a blood vessel, comprising:
an anchoring system having a first portion and a second portion which is spaced apart from the first portion in a first direction; and
a cushioning member located between the first and second portions of the anchoring system such that movement of a portion of the cushioning member in a second direction, which is orthogonal to the first direction, is not constrained by the anchoring system, and wherein the cushioning member is configured to absorb pulsatile energy transmitted by blood flowing with the vessel.

149. The device of example 148 wherein the cushioning member is elastically deformable and is configured to expand in response to an increase of blood pressure within the vessel, and relax as the blood pressure within the vessel subsequently decreases.

150. A device for treating a blood vessel, comprising:
an endovascular cushioning device having a proximal anchor and a distal anchor which is spaced apart from the proximal anchor, each of the proximal and distal anchors being configured to abut against an inner wall of a major artery; and
an elastically deformable member extending between the proximal and distal anchors, wherein the elastically deformable member is configured to expand in response to an increase of blood pressure within the vessel, and relax as the blood pressure within the vessel subsequently decreases.

151. The device of example 150 wherein a portion of the elastically deformable membrane located longitudinally between the proximal and distal anchors defines a region of reduced internal cross-sectional area relative to the proximal and distal anchors when the elastically deformable membrane is radially relaxed.

152. The device of example 150 or example 151 wherein the proximal and distal anchors are each radially expandable between a first diameter before deployment and a second diameter after deployment.

153. The device of any one of examples 150-152, further comprising one or more threads secured to the proximal anchor.

154. The device of example 153 wherein each thread is secured to an eyelet.

155. A device for treating an artery selected from a left common carotid artery, a right common carotid artery, a brachiocephalic artery, the ascending aorta, an internal carotid artery, or an abdominal aorta, the device comprising:
a wrap fabricated from an elastically deformable material, and
an engagement formation adapted to secure two opposing edges of the wrap around the artery,
wherein the elastically deformable material is configured to radially expand during a systole stage and radially contract during a diastole stage.

156. The device of example 155 wherein, when the wrap is in position around the artery, the wrap entirely or substantially entirely surrounds the artery over a portion of its length.

157. The device of example 155 wherein the engagement formation includes sutures and/or staples.

158. The device of example 155 wherein the engagement formation includes a zip lock.

159. A device for treating a left common carotid artery, a right common carotid artery, a brachiocephalic artery, or an ascending aorta, the device comprising:
a proximal anchor configured to be wrapped around the artery;
a distal anchor configured to be wrapped around the artery and longitudinally spaced relative to the proximal anchor; and
a helical band adapted to be wound around the artery, the helical band having a first end securable to the proximal anchor and an opposing second end securable to the distal anchor, wherein the helical band is adapted to radially expand during a systole stage and radially contract during a diastole stage.

160. The device of example 159 wherein the first end of the helical band is secured to the proximal anchor and the second end of the helical band is secured to the distal anchor.

161. A device for treating or slowing the effects of dementia, comprising:
a damping member comprising a deformable, generally tubular sidewall having an outer surface and an inner surface that is undulating in a longitudinal direction, and wherein the sidewall is configured to be positioned in apposition with a blood vessel wall to absorb pulsatile energy transmitted by blood flowing through the blood vessel.

162. The device of example 161 wherein the damping member is configured to be positioned in apposition with at least one of a left common carotid artery, a right common carotid artery, and a brachiocephalic artery.

163. The device of example 161 wherein the damping member is configured to be positioned in apposition with an ascending aorta.

164. The device of any one of examples 161-163 wherein the damping member is configured to be positioned in apposition with an inner surface of the blood vessel wall.

165. The device of any one of examples 161-163 wherein the damping member is configured to be positioned in apposition with an outer surface of the blood vessel wall.

166. The device of any one of examples 161-165 wherein the sidewall has an inner diameter, and, when the damping member is in a deployed state, the inner diameter increases then decreases in an axial direction.

167. The device of any one of examples 161-166 wherein the cross-sectional area decreases then increases in longitudinal direction.

168. The device of any one of examples 161-167 wherein the outer surface has a generally cylindrical shape.

169. The device of any one of examples 161-167 wherein the outer surface has an undulating shape.

170. The device of any one of examples 161-169, further comprising an anchoring member coupled to the damping member and axially aligned with only a portion of the damping member, wherein the anchoring member is configured to engage the blood vessel wall and secure the damping member to the blood vessel wall.

171. The device of example 170 wherein the anchoring member is a first anchoring member and the device further comprises a second anchoring member coupled to the damping member, and wherein the second anchoring member:
is axially aligned with only a portion of the damping member, and
is spaced apart from the first anchoring member along the longitudinal axis of the damping member.

172. The device of any one of examples 161-171 wherein, when the damping member is positioned adjacent the blood vessel wall, the damping member does not constrain the diameter of the blood vessel wall.

173. A device for treating or slowing the effects of dementia, comprising:
an elastic member which is configured to abut an arterial wall and form a generally tubular structure having an inner diameter, an outer diameter, an outer surface, and an undulating inner surface, and wherein at least one of the outer diameter and the inner diameter increases and decreases in response to an increase and a decrease in pulse pressure within the blood vessel, respectively.

174. The device of example 173 wherein the elastic member is configured to be positioned in apposition with at least one of a left common carotid artery, a right common carotid artery, and a brachiocephalic artery.

175. The device of example 173 wherein the elastic member is configured to be positioned in apposition with an ascending aorta.

176. The device of any one of examples 173-175 wherein the elastic member is configured to be positioned in apposition with an inner surface of the blood vessel wall.

177. The device of any one of examples 173-175 wherein the elastic member is configured to be positioned in apposition with an outer surface of the blood vessel wall.

178. The device of any one of examples 173-177 wherein the sidewall has an inner diameter, and, when the elastic member is in a deployed state, the inner diameter increases then decreases in an axial direction.

179. The device of any one of examples 173-178 wherein the cross-sectional area decreases then increases in longitudinal direction.

180. The device of any one of examples 173-179 wherein the outer surface has a generally cylindrical shape.

181. The device of any one of examples 173-179 wherein the outer surface has an undulating shape.

182. The device of any one of examples 173-181, further comprising an anchoring member coupled to the elastic member and axially aligned with only a portion of the elastic member, wherein the anchoring member is configured to engage the blood vessel wall and secure the elastic member to the blood vessel wall.

183. The device of example 182 wherein the anchoring member is a first anchoring member and the device further comprises a second anchoring member coupled to the elastic member, and wherein the second anchoring member:
  is axially aligned with only a portion of the elastic member, and
  is spaced apart from the first anchoring member along the longitudinal axis of the elastic member.

184. The device of any one of examples 173 to 23 wherein, when the elastic member is positioned adjacent the blood vessel wall, the elastic member does not constrain the diameter of the blood vessel wall.

185. The device of any one of examples 173-184 wherein the damping member or elastic member has a low-profile state and a deployed state.

186. The device of example 185 wherein the deployed state is for delivery to a treatment site at a blood vessel wall.

187. The device of example 185 or 186 wherein the damping member or elastic member has a first, lesser outer diameter when in the low-profile state and a second, greater diameter when in the deployed state.

188. A device for treating or slowing the effects of dementia, comprising:
  a damping member including an abating substance, wherein the damping member forms a generally tubular structure having an axis, wherein the abating substance is able to move axially relative to the tubular structure, and wherein the damping member is configured to be positioned along the circumference of an artery such that, when a pulse wave traveling through the artery applies a stress at a first axial location along the length of the tubular structure, at least a portion of the abating substance moves away from the first location to a second axial location along the length of the tubular structure.

189. The device of example 188, wherein the abating substance comprises a quantity of a fluid and/or gel comprising particles, contained within a flexible member, and the particles may move axially relative to the tubular structure within the flexible member.

190. The device of example 189 wherein the flexible member may, at at least some locations along the length of the tubular structure, be deformed radially with respect to the tubular structure.

191. The device of any one of examples 188-190, further comprising a structural element coupled to the damping member.

192. The device of any one of examples 188-191 wherein, in a deployed state, the damping member is configured to wrap around at least a portion of the circumference of the artery.

193. The device of example 192 wherein the damping member includes a break along its length, to allow it to be fitted around the portion of the circumference of the artery.

194. The device of example 193, further comprising cooperating sealing arrangements located on or near opposing edges of the break, to allow the edges to be joined together once the damping member has been fitted around the portion of the circumference of the artery.

195. The device of any one of examples 188-194 wherein, in a deployed state, the device has a pre-set helical configuration.

196. The device of any one of examples 188-195 wherein the damping member includes a liquid.

197. The device of any one of examples 188-196 wherein the damping member includes a gas.

198. The device of any one of examples 188-197 wherein the damping member includes a gel.

199. The device of any one of examples 188-198 wherein the damping member, in a deployed configuration, is configured to be positioned in apposition with an outer surface of the arterial wall.

200. The device of any one of examples 188-199 wherein the damping member, in a deployed configuration, is configured to be positioned around the arterial wall such that an inner surface of the damping member is in contact with blood flowing through the artery.

201. A device for treating or slowing the effects of dementia, comprising:
  wherein the fluid particles are able to move axially along at least a part of the length of the damping structure, the damping member being configured to be positioned along the circumference of an artery at a treatment site along a length of the artery,
  wherein, when the damping member is in a deployed configuration and positioned at the treatment site, a wavefront traveling through the length of the artery redistributes at least a portion of the fluid particles along the length of the damping member such that the inner diameter of the damping member increases at the axial location along the damping member aligned with the wavefront while the inner diameter of the damping member at another axial location along the damping member decreases.

202. The device of example 201 wherein the fluid particles are contained within a flexible member, and the particles may move along the length of the damping member within the flexible member.

203. The device of example 202 wherein the flexible member may, at at least some locations along the length of the damping member, be deformed radially with respect to the damping member.

204. The device of any one of examples 201-203, further comprising a structural element coupled to the damping member.

205. The device of any one of examples 201-204 wherein, in the deployed state, the damping member is configured to wrap around at least a portion of the circumference of the artery.

206. The device of example 205 wherein the damping member includes a break along its length, to allow it to be fitted around the portion of the circumference of the artery.

207. The device of example 206, further comprising cooperating sealing arrangements located on or near opposing edges of the break, to allow the edges to be joined together once the damping member has been fitted around the portion of the circumference of the artery.

208. The device of any one of examples 201-207 wherein, in the deployed state, the device has a pre-set helical configuration.

209. The device of any one of examples 201-208 wherein the damping member includes a liquid.

210. The device of any one of examples 201-209 wherein the damping member includes a gas.

211. The device of any one of examples 201-210 wherein the damping member includes a gel.

212. The device of any one of examples 201-211 wherein the damping member, in the deployed configuration, is configured to be positioned in apposition with an outer surface of the arterial wall.

213. The device of any one of examples 201-212 wherein the damping member, in the deployed configuration, is configured to be positioned around the arterial wall such that an inner surface of the damping member is in contact with blood flowing through the artery.

214. The device of any one of examples 201-213 wherein the damping member has a low profile configuration and a deployed configuration.

V. CONCLUSION

Although many of the embodiments are described above with respect to systems, devices, and methods for treating and/or slowing the progression of vascular and/or age-related dementia via intravascular methods, the technology is applicable to other applications and/or other approaches, such as surgical implantation of one or more damping devices and/or treatment of blood vessels other than arterial blood vessels supplying blood to the brain, such as the abdominal aorta. Any appropriate site within a blood vessel may be treated including, for example, the ascending aorta, the aortic arch, the brachiocephalic artery, the right subclavian artery, the left subclavian artery, the left common carotid artery, the right common carotid artery, the internal and external carotid arteries, and/or branches of any of the foregoing. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2A-19B.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A method of treating an artery, comprising:
positioning a damping device along the artery so that (a) a structural member of the damping device has a helical shape about the artery and (b) a damping member of the damping device at least partially contacts an outer surface of the artery;
wherein the damping member is coupled to the structural member; and
wherein the damping member and/or the structural member deforms in response to a wavefront of blood passing through the artery and thereby attenuates energy of the wavefront.

2. The method of claim 1 wherein positioning the damping device along the artery further includes wrapping the damping device around a circumference of the artery.

3. The method of claim 2 wherein:
the damping device has a first end, a second end, and longitudinal edges; and
wrapping the damping device around the circumference of the artery includes wrapping the damping device around the artery such that the longitudinal edges oppose one another and form a slot extending from the first end to the second end.

4. The method of claim 3 wherein the slot is helical.

5. The method of claim 1 wherein the structural member is formed of metal, and wherein the damping member is formed of a flexible material.

6. The method of claim 1 wherein the structural member is formed of nitinol, and wherein the damping member is formed of silicone.

7. The method of claim 1 wherein the structural member is pre-set to have the helical shape in a relaxed configuration.

8. The method of claim 1 wherein the structural member is configured to remain substantially unchanged when the damping member deforms in response to the wavefront of blood passing through the artery.

9. The method of claim 1 wherein the artery is a carotid artery.

10. The method of claim 1 wherein the artery is a brachiocephalic trunk.

11. The method of claim 1 wherein the artery is a right common carotid artery.

12. The method of claim 1 wherein the artery is an ascending aorta.

13. The method of claim 1 wherein the damping member is elastic and expands during systole and contracts during diastole.

14. The method of claim 1 wherein the damping member includes an abating substance configured to deform in response to the wavefront of blood passing through the artery and thereby attenuate the energy of the wavefront.

15. A method of treating an artery, comprising:
  wrapping a damping device around at least a portion of a circumference of an exterior surface of the artery so that (a) a structural member of the damping device has a helical shape about the artery and (b) an inner surface of a damping member of the damping device at least partially contacts the exterior surface of the artery;
  wherein the damping member is coupled to the structural member;
  wherein the damping device has a first end, a second end, and longitudinal edges that oppose one another and form a slot from the first end to the second end after the damping device has been wrapped around the artery; and
  wherein the damping member deforms in response to a wavefront of blood passing through the artery and thereby attenuates energy of the wavefront.

16. The method of claim 15 wherein the structural member is formed of metal, and wherein the damping member is formed of a flexible material.

17. The method of claim 15 wherein the structural member is formed of nitinol, and wherein the damping member is formed of silicone.

18. The method of claim 15 wherein the structural member is pre-set to have the helical shape in a relaxed configuration.

19. The method of claim 15 wherein the slot is helical after the damping device has been wrapped around the artery.

* * * * *